(12) United States Patent
Sun et al.

(10) Patent No.: US 11,554,272 B2
(45) Date of Patent: Jan. 17, 2023

(54) SYSTEM AND METHOD FOR DIAGNOSTIC AND TREATMENT

(71) Applicant: SHANGHAI UNITED IMAGING HEALTHCARE CO., LTD., Shanghai (CN)

(72) Inventors: Haining Sun, Shanghai (CN); Guotao Quan, Shanghai (CN); Yuan Bao, Shanghai (CN); Wenjing Cao, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 348 days.

(21) Appl. No.: 16/944,280

(22) Filed: Jul. 31, 2020

(65) Prior Publication Data
US 2020/0360730 A1    Nov. 19, 2020

Related U.S. Application Data

(63) Continuation of application No. 16/222,151, filed on Dec. 17, 2018, now Pat. No. 10,765,890, which is a
(Continued)

(51) Int. Cl.
*G06K 9/00*     (2022.01)
*A61B 6/00*     (2006.01)
(Continued)

(52) U.S. Cl.
CPC ......... *A61N 5/1067* (2013.01); *A61N 5/1039* (2013.01); *G06T 5/002* (2013.01);
(Continued)

(58) Field of Classification Search
CPC .............. G06K 9/00; A61B 6/00; G06F 19/00
(Continued)

(56) References Cited

U.S. PATENT DOCUMENTS 9,730,660 B2    8/2017    Suzuki
2005/0220265 A1*  10/2005  Besson ................... G21K 1/10
                                                       378/16
(Continued)

FOREIGN PATENT DOCUMENTS

CN    106683146 A    5/2017
CN    103971387 B   10/2017
WO    2019019199 A1  1/2019

OTHER PUBLICATIONS

International Search Report in PCT/CN2017/110005 dated Aug. 8, 2018, 5 pages.
(Continued)

*Primary Examiner* — Seyed H Azarian
(74) *Attorney, Agent, or Firm* — Metis IP LLC

(57) ABSTRACT

A method may include obtaining first image data relating to a region of interest (ROI) of a first subject. The first image data corresponding to a first equivalent dose level may be acquired by a first device. The method may also include obtaining a model for denoising relating to the first image data and determining second image data corresponding to an equivalent dose level higher than the first equivalent dose level based on the first image data and the model for denoising. In some embodiments, the method may further include determining information relating to the ROI of the first subject based on the second image data and recording the information relating to the ROI of the first subject.

20 Claims, 16 Drawing Sheets

Related U.S. Application Data continuation of application No. PCT/CN2017/110005, filed on Nov. 8, 2017.

(51) Int. Cl.

| | | |
|---|---|---|
| *A61N 5/10* | (2006.01) |
| *G06T 5/00* | (2006.01) |
| *G06T 5/50* | (2006.01) |
| *G06T 11/00* | (2006.01) |
| *G06T 7/00* | (2017.01) |
| *G16H 50/20* | (2018.01) |
| *G16H 30/20* | (2018.01) |
| *G06V 10/24* | (2022.01) |

(52) U.S. Cl.
CPC .............. *G06T 5/50* (2013.01); *G06T 7/0014* (2013.01); *G06T 11/00* (2013.01); *G06T 11/006* (2013.01); *G06T 11/008* (2013.01); *G06V 10/24* (2022.01); *G16H 30/20* (2018.01); *G16H 50/20* (2018.01); *G06T 2207/10081* (2013.01); *G06T 2207/20081* (2013.01); *G06T 2207/20084* (2013.01); *G06T 2207/30196* (2013.01); *G06T 2211/424* (2013.01)

(58) Field of Classification Search
USPC ........ 382/100, 103, 106–107, 128–133, 154, 382/162, 168, 172–173, 181, 189, 199, 382/219, 224, 232, 254, 260, 274–276, 382/286–291, 305; 378/4, 21, 16, 37
See application file for complete search history.

(56) References Cited

U.S. PATENT DOCUMENTS

| | | | |
|---|---|---|---|
| 2011/0124976 A1 | 5/2011 | Sabczynski et al. | |
| 2013/0089252 A1 | 4/2013 | Shechter | |
| 2015/0196265 A1* | 7/2015 | Suzuki ................. | A61B 6/5211 378/37 |
| 2015/0201895 A1 | 7/2015 | Suzuki | |
| 2016/0063686 A1 | 3/2016 | Lou et al. | |
| 2017/0071562 A1 | 3/2017 | Suzuki | |
| 2017/0189719 A1 | 7/2017 | Liu et al. | |
| 2017/0189720 A1 | 7/2017 | Liu et al. | |
| 2017/0189724 A1 | 7/2017 | Liu et al. | |
| 2018/0018757 A1* | 1/2018 | Suzuki ................. | G06T 3/4053 |
| 2018/0144466 A1* | 5/2018 | Hsieh ................... | G06T 7/0012 |
| 2018/0268526 A1* | 9/2018 | Mentl ................... | G06T 11/008 |
| 2019/0133544 A1 | 5/2019 | Liu et al. | |
| 2020/0041669 A1 | 2/2020 | Dong | |
| 2020/0097773 A1* | 3/2020 | Hsieh ................... | G06T 7/0012 |

OTHER PUBLICATIONS

Written Opinion in PCT/CN2017/110005 dated Aug. 8, 2018, 4 pages.
First Office Action in Chinese Application No. 201811326758.9 dated Mar. 2, 2020, 15 pages.

* cited by examiner

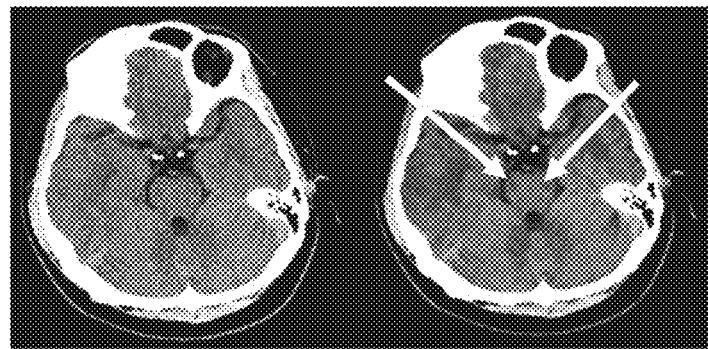
FIG. 18A      FIG. 18B
 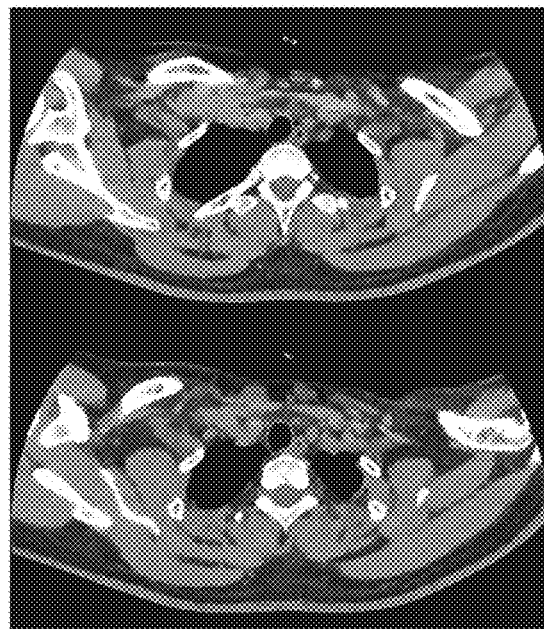
FIG. 19A      FIG. 19B

SYSTEM AND METHOD FOR DIAGNOSTIC AND TREATMENT

CROSS REFERENCE TO RELATED APPLICATION

This present application is a continuation of U.S. application Ser. No. 16/222,151 filed on Dec. 17, 2018, which is a continuation of International Application No. PCT/CN2017/110005 filed on Nov. 8, 2017, the entire contents of which are incorporated herein by reference.

TECHNICAL FIELD

The present disclosure generally relates to a medical diagnostic and treatment system, and more specifically relates to methods and systems for decreasing dosage in a radiotherapy procedure.

BACKGROUND

Various imaging techniques have been used in medical diagnosis, radiation therapy planning, surgery planning, and other medical procedures, such as X-ray photography, magnetic resonance imaging (MRI), computed tomography (CT), positron emission tomography (PET), etc. For example, the CT-based image-guided radiotherapy (IGRT) has been widely used in radiation therapy. Conventionally, a radiation therapy treatment plan (also referred to as a treatment plan) for a patient is generated before the treatment starts. The treatment plan may be delivered to the patient during several treatment fractions spread over a treatment period of multiple days. During the treatment period, one or more IGRT images (e.g., a CT image) may be used to determine and/or position a region of interest (ROI) (e.g., a cancer). However, an IGRT image generated based on low-dose projection data may show noise and/or artifacts (e.g., staircase artifacts). The artifacts may reduce the image quality and influence the results of diagnosis made on the basis of such an image. A high-dose IGRT scan may at least partially alleviate these problems but at the cost of exposing a scanned patient to too more radiation. It is desirable to provide systems and methods for generating a high-dose image of improved quality, based on a low-dose scan.

SUMMARY

According to an aspect of the present disclosure, a method for processing image data is provided. The method may be implemented on at least one machine each of which has at least one processor and storage. The method may include obtaining first image data relating to a region of interest (ROI) of a first subject. The first image data may correspond to a first equivalent dose level. The method may further include obtaining a model for denoising relating to the first image data and determining second image data corresponding to an equivalent dose level higher than the first equivalent dose level based on the first image data and the model for denoising. In some embodiments, the method may include determining information relating to the ROI of the first subject based on the second image data and recording the information relating to the ROI of the first subject.

In some embodiments, the model for denoising may include a first neural network model for denoising. Multiple groups of training data relating to multiple second subjects may be obtained. Each group of the multiple groups of training data may relate to a second subject and each of the multiple groups of training data may include third image data corresponding to a third equivalent dose level and fourth image data corresponding to a fourth equivalent dose level lower than the third equivalent dose level. The first neural network model for denoising may be obtained by training a neural network model based on the multiple groups of training data.

In some embodiments, the model for denoising may include a first neural network model for denoising. Multiple groups of training data relating to multiple second subjects may be obtained. Each group of the multiple groups of training data may relate to a second subject and each of the multiple groups of training data may include third image data corresponding to a third equivalent dose level and fourth image data corresponding to a fourth equivalent dose level lower than the third equivalent dose level. A second neural network model for denoising may be obtained by training a neural network model based on the multiple groups of training data. Fifth image data relating to the first subject may be obtained. The fifth image data may correspond to a fifth equivalent dose level higher than the first equivalent dose level. The first neural network model for denoising may be obtained by training the second neural network model for denoising based on the fifth image data.

In some embodiments, the first image data may be acquired by a first device, and the fourth image data may be acquired by the first device.

In some embodiments, the first image data may be acquired by a first device, and the fourth image data may be acquired by a second device different from the first device.

In some embodiments, at least one of the first image data or the fourth image data may be preprocessed.

In some embodiments, the determining, based on the first image data and the model for denoising, second image data corresponding to a second equivalent dose level higher than the first equivalent dose level, may further include determining, based on the model for denoising and the first image data, noise data included in the first image data; and determining, based on the noise data and the first image data, the second image data.

In some embodiments, the model for denoising may include an image reconstruction model using an iterative reconstruction algorithm.

In some embodiments, the image reconstruction model may include a first statistical model of noises in a projection domain. The first image data may include first projection data. The first projection data may be processed based on the first statistical model of noises in the projection domain to obtain second projection data. A first image may be generated based on the second projection data. A second statistical model of noises in an image domain may be generated based on the first statistical model of noises. The second image data including a second image relating to the ROI of the subject may be determined based on the first image and the second statistical model of noises.

In some embodiments, the first image data may include first projection data. The second image data may include a target image relating to the ROI of the first subject. Third projection data indicating a difference between the first projection data and second projection data corresponding to an image estimation may be determined. Fourth projection data may be determined based on the third projection data and the first statistical model of noises. An error image relating to the ROI of the first subject may be generated based on the fourth projection data. The target image relating to the ROI of the first subject may be determined based on the error image and a second statistical mode of noises.

In some embodiments, a value of an objective function in each iteration may be determined iteratively based on the error image and the second statistical mode of noises. An image estimation after each iteration may be updated based on the value of the objective function obtained in a most recent iteration. The target image may be determined until a condition is satisfied.

In some embodiments, the objective function may further include a first regularization item for suppressing noises.

In some embodiments, the objective function may further include a second regularization item for suppressing artifact. The second regularization item may be associated with sparsity of the first projection data.

In some embodiments, the first equivalent dose level may be no less than 15% of the second equivalent dose level.

In some embodiments, the first equivalent dose level may be no less than 50% of the second equivalent dose level.

In some embodiments, the first equivalent dose level may be no less than 85% of the second equivalent dose level.

In some embodiments, the first image data may be acquired by a computed tomography (CT), and a ratio of the first equivalent dose level to the second equivalent dose level may be equal to 1:7.

In some embodiments, the first image data may be acquired by a cone beam computed tomography (CBCT), and a ratio of the first equivalent dose level to the second equivalent dose level may be equal to 1:3.

In some embodiments, the first device may further include a radiotherapy treatment (RT) device According to an aspect of the present disclosure, a system for processing image data is provided. The system may include a computer-readable storage medium storing executable instructions and at least one processor in communication with the computer-readable storage medium. When the executable instructions are executed, the executable instructions may cause the system to implement a method. The method may include obtaining first image data relating to a region of interest (ROI) of a first subject. The first image data may correspond to a first equivalent dose level. The method may further include obtaining a model for denoising relating to the first image data and determining second image data corresponding to an equivalent dose level higher than the first equivalent dose level based on the first image data and the model for denoising. In some embodiments, the method may include determining information relating to the ROI of the first subject based on the second image data and recording the information relating to the ROI of the first subject.

According to another aspect of the present disclosure, a non-transitory computer readable medium is provided. The non-transitory computer readable medium may include executable instructions. When the instructions are executed by at least one processor, the instructions may cause the at least one processor to implement a method. The method may include obtaining first image data relating to a region of interest (ROI) of a first subject. The first image data may correspond to a first equivalent dose level. The method may further include obtaining a model for denoising relating to the first image data and determining second image data corresponding to an equivalent dose level higher than the first equivalent dose level based on the first image data and the model for denoising. In some embodiments, the method may include determining information relating to the ROI of the first subject based on the second image data and recording the information relating to the ROI of the first subject.

According to an aspect of the present disclosure, a system for processing image data is provided. The system may include a data acquisition module configured to obtain first image data relating to a region of interest (ROI) of a first subject. The first image data may correspond to a first equivalent dose level. The system may further include a model generation module configured to obtain a model for denoising relating to the first image data. The system may further include an image data processing module configured to determine second image data corresponding to an equivalent dose level higher than the first equivalent dose level based on the first image data and the model for denoising, determining information relating to the ROI of the first subject based on the second image data, and recording the information relating to the ROI of the first subject.

According to an aspect of the present disclosure, an image-guided radiotherapy (IGRT) method is provided. The method may include obtaining first information relating to a region of interest (ROI) of a first subject from a treatment plan of the first subject; obtaining first image data relating to the region of interest (ROI) of the first subject, the first image data corresponding to a first equivalent dose level; obtaining a model for denoising relating to the first image data; determining, based on the first image data and the model for denoising, second image data corresponding to an equivalent dose level higher than the first equivalent dose level; determining, based on the second image data, second information relating to the ROI of the first subject; and adjusting, based on a comparison between the second information relating to the ROI and the first information relating to the ROI, a position of the subject in space.

In some embodiments, the model for denoising may include a first neural network model for denoising, and the obtaining a model for denoising, may further include obtaining multiple groups of training data relating to multiple second subjects, each group of the multiple groups of training data relating to a second subject, each of the multiple groups of training data including third image data corresponding to a third equivalent dose level and fourth image data corresponding to a fourth equivalent dose level lower than the third equivalent dose level; training, based on the multiple groups of training data, a neural network model to obtain a second neural network model for denoising; obtaining fifth image data relating to the first subject, the fifth image data corresponding to a fifth equivalent dose level higher than the first equivalent dose level; and training, based on the fifth image data relating to the first subject, the second neural network model for denoising to obtain the first neural network model for denoising.

In some embodiments, the model for denoising may include an image reconstruction model using an iterative reconstruction algorithm.

According to an aspect of the present disclosure, a method for radiation delivery is provided. The method may include obtaining first image data relating to a region of interest (ROI) of a first subject before or during or after a treatment, the first image data corresponding to a first equivalent dose level; obtaining a model for denoising relating to the first image data; determining, based on the first image data and the model for denoising, second image data corresponding to an equivalent dose level higher than the first equivalent dose level; determining, based on the second image data, information relating to the ROI of the first subject; and modifying, based on a comparison between the determined information relating to the ROI and information relating to the ROI in a treatment plan of the first subject, the treatment plan of the first subject.

According to an aspect of the present disclosure, a method for radiation delivery is provided. The method may include obtaining first image data relating to a region of interest (ROI) of a first subject before or during or after a treatment, the first image data corresponding to a first equivalent dose level; obtaining a model for denoising relating to the first image data; determining, based on the first image data and the model for denoising, second image data corresponding to an equivalent dose level higher than the first equivalent dose level; determining, based on the second image data, first information relating to the ROI of the first subject; comparing the first information relating to the ROI of the first subject and second information relating to the ROI in a treatment plan of the first subject; and performing a delivery of treatment radiation beam based on the comparison, including at least one of deactivating a delivery of treatment radiation beam in response to a determination that the comparison is outside a range; or reactivating a delivery of treatment radiation beam in response to a determination that the comparison is within the range.

According to an aspect of the present disclosure, a planning method for a treatment is provided. The method may include obtaining first image data relating to a region of interest (ROI) of a subject, the first image data corresponding to a first equivalent dose level; obtaining a model for denoising relating to the first image data; determining, based on the first image data and the model for denoising, second image data corresponding to an equivalent dose level higher than the first equivalent dose level; determining, based on the second image data, information relating to the ROI of the first subject; and determining, based on the information relating to the ROI, a treatment plan of the subject Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIGS. 18A and 18B illustrate exemplary images corresponding to the same dose level generated based on different reconstruction algorithms according to some embodiments of the present disclosure; and FIGS. 19A and 19B illustrate exemplary images corresponding to the same dose level generated based on different reconstruction algorithms according to some embodiments of the present disclosure.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, section or assembly of different level in ascending order. However, the terms may be displaced by another expression if they achieve the same purpose.

Figure 2:
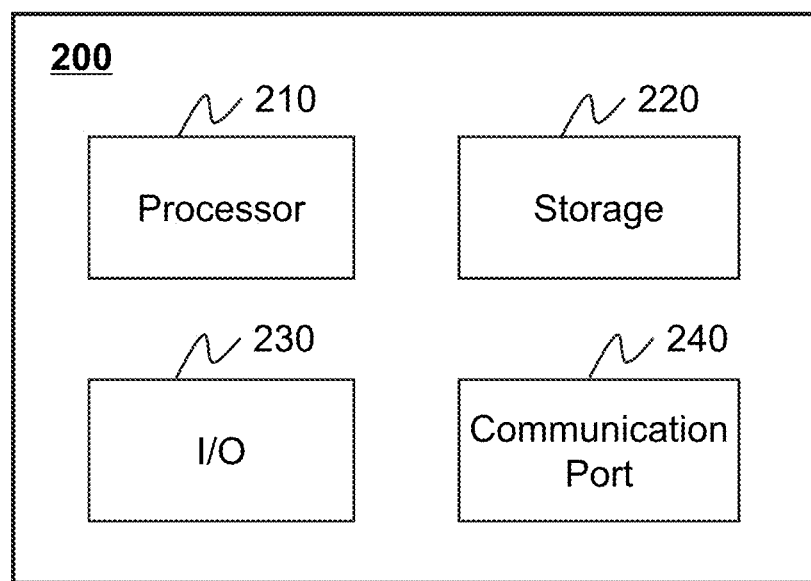
FIG. 2 is a schematic diagram illustrating exemplary hardware and/or software components of an exemplary computing device on which the processing device may be implemented according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or themselves, and/or may be invoked in response to detected events or interrupts. Software modules/units/blocks configured for execution on computing devices (e.g., processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may apply to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The flowcharts used in the present disclosure illustrate operations that systems implement according to some embodiments of the present disclosure. It is to be expressly understood, the operations of the flowcharts may be implemented not in order. Conversely, the operations may be implemented in inverted order, or simultaneously. Moreover, one or more other operations may be added to the flowcharts. One or more operations may be removed from the flowcharts.

Provided herein are systems and components for medical diagnostic and/or treatment. In some embodiments, the medical system may include a diagnostic and treatment system. The diagnostic and treatment system may include a treatment plan system (TPS), an image-guide radio therapy (IGRT) system (e.g., an CT guided radiotherapy system), etc.

An aspect of the present disclosure relates to a system and method for processing image data. The system may process first image data relating to an ROI of a subject corresponding to a first equivalent dose level based on a model for denoising to obtain second image data. The second image data may correspond to an equivalent dose level higher than the first equivalent dose level. In some embodiments, the model for denoising may include a neural network model for denoising. Further, the first image data may be processed based on the neural network model for denoising to obtain noise data. The second image data may be determined based on the first image data and the noise data. In some embodiments, the model for denoising may include an iterative reconstruction model. The second image data may be determined based on the iterative reconstruction model using an iterative reconstruction algorithm.

It should be noted that the diagnostic and treatment system 100 described below is merely provided for illustration purposes, and not intended to limit the scope of the present disclosure. For persons having ordinary skills in the art, a certain amount of variations, changes, and/or modifications may be deducted under the guidance of the present disclosure. Those variations, changes, and/or modifications do not depart from the scope of the present disclosure.

Figure 1:
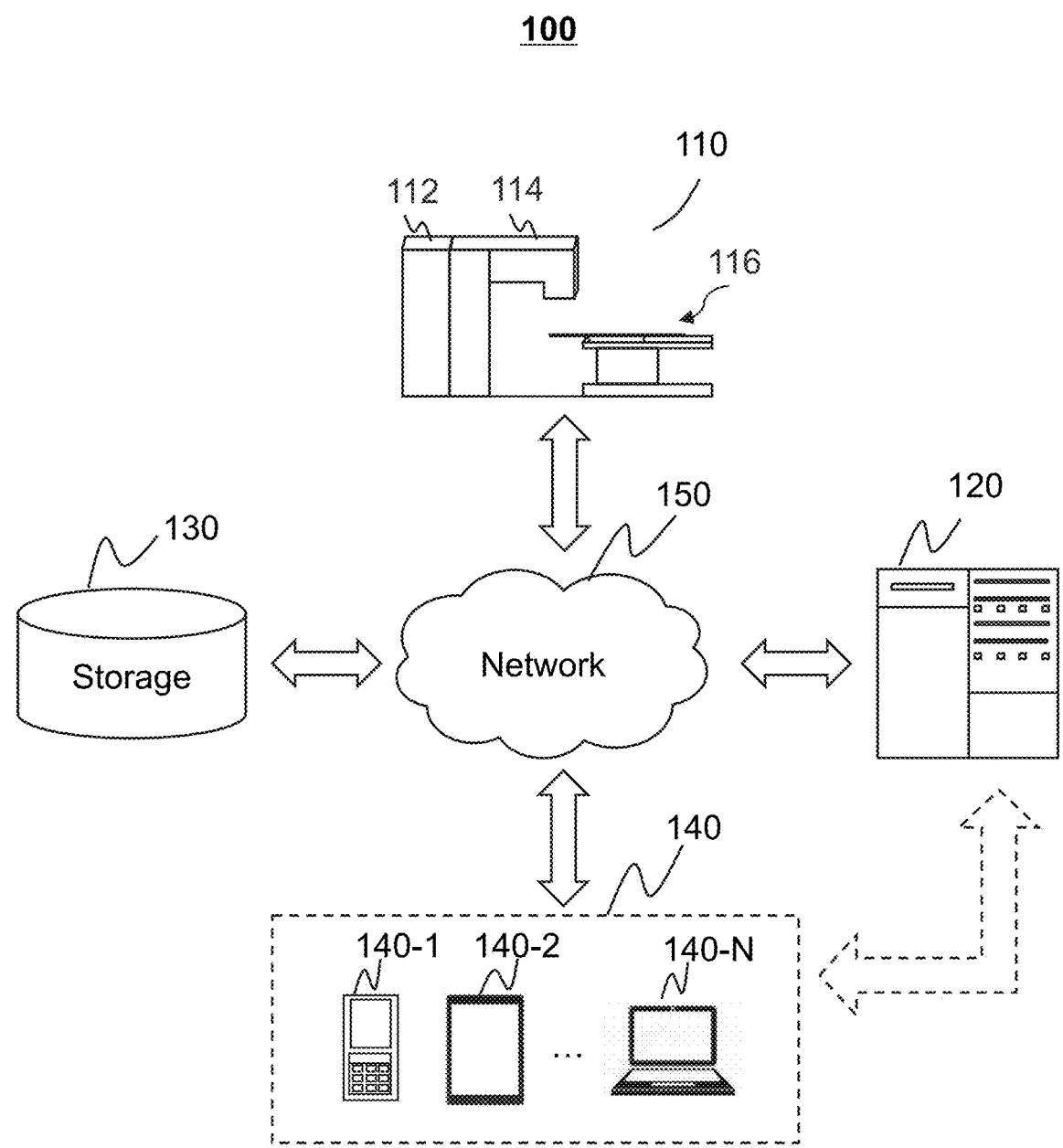
FIG. 1 is a schematic diagram illustrating an exemplary diagnostic and treatment system according to some embodiments of the present disclosure.

FIG. 1 is a schematic diagram illustrating an exemplary diagnostic and treatment system 100 according to some embodiments of the present disclosure. As shown, the diagnostic and treatment system 100 may include an image guided radio therapy (IGRT) apparatus 110, a processing device 120, storage 130, one or more terminal(s) 140, and a network 150. In some embodiments, the IGRT apparatus 110, the processing device 120, the storage 130, and/or the terminal(s) 140 may be connected to and/or communicate with each other via a wireless connection (e.g., the network 150), a wired connection, or a combination thereof. The connections between the components in the diagnostic and treatment system 100 may vary. Merely by way of example, the IGRT apparatus 110 may be connected to the processing device 120 through the network 150, as illustrated in FIG. 1. As another example, the IGRT apparatus 110 may be connected to the processing device 120 directly. As a further example, the storage 130 may be connected to the processing device 120 through the network 150, as illustrated in FIG. 1, or connected to the processing device 120 directly. As still a further example, the terminal(s) 140 may be connected to the processing device 120 through the network 150, as illustrated in FIG. 1, or connected to the processing device 120 directly (as indicated by the bidirectional arrow in dashed line shown in FIG. 1).

The IGRT apparatus 110 may be a multi-modality (e.g., two-modality) apparatus to acquire a medical image relating to at least one part of a subject and perform radiotherapy treatment on the at least one part of the subject. In some embodiments, the medical image may be a two-dimensional (2D) image, a three-dimensional (3D) image, a four-dimensional (4D) image, or the like, or a combination thereof. The subject may be biological or non-biological. For example, the subject may include a patient, a man-made object, etc. As another example, the subject may include a specific portion, organ, and/or tissue of the patient. For example, the subject may include head, neck, thorax, cardiac, stomach, blood vessel, soft tissue, tumor, nodules, or the like, or a combination thereof. In some embodiments, the subject may include a region of interest (ROI), such as a tumor, a node, etc.

In some embodiments, the IGRT apparatus 110 may include an imaging device 112, a treatment device 114, and a couch 116. The imaging device 112 may be configured to provide image data via scanning a subject, or a part of the subject. In some embodiments, the imaging device 112 may include a single-modality scanner and/or multi-modality scanner. The single-modality may include, for example, a computed tomography (CT) scanner, a cone beam CT (CBCT), etc. The multi-modality scanner may include a single photon emission computed tomography-computed tomography (SPECT-CT) scanner, a positron emission tomography-computed tomography (PET-CT) scanner, a computed tomography-ultra-sonic (CT-US) scanner, a digital subtraction angiography-computed tomography (DSA-CT) scanner, a computed tomography-magnetic resonance (CT-MR) scanner, or the like, or a combination thereof. In some embodiments, the image data may include projection data, images relating to the subject, etc. The projection data may be raw data generated by the imaging device 112 by scanning the subject, or data generated by a forward projection on an image relating to the subject.

In some embodiments, the imaging device 112 may include an imaging radiation source, a detector, etc. The imaging radiation source may generate and/or emit one or more radiation beams toward the subject according to one or more scanning parameters. The detector of the imaging device 112 may include one or more detector units that may detect a distribution of the radiation beams emitted from the imaging radiation source. In some embodiments, the detector of the imaging device 112 may be connected to a data conversation circuit configured to convert the distribution of the detected radiation beams into image data (e.g., projection data). The image data may correspond to the dose level of a detected radiation beams. In some embodiments, the dose level of the detected radiation beams may include noise represented in the image data. For example, the higher the dose level of radiation is, the lower the noise level relative to true signal (reflecting actual anatomy) represented in the image data may be. The lower the dose-level of radiation is, the higher the noise level relative to true signal represented in the image data may be. As used herein, the dose level of the radiation may be defined by a CT dose index (CTDI), an effective dose, a dose-length product, etc. The CT dose index (CTDI) may refer to the radiation energy of radiation corresponding to a single slice along a long axis (e.g., the axial direction) of the imaging device 112. The dose-length product may refer to the total radiation energy of radiation received by a subject being examined in an integrated scanning procedure. The effective dose may refer to the radiation energy of radiation received by a specific region of a subject in an integrated scanning procedure.

The treatment device 114 may be configured to perform radiotherapy on at least one part of the subject (e.g., an ROI) according to the medical image and other information. The treatment device 114 may include a treatment radiation source. The treatment radiation source may emit treatment radiations towards the subject. Exemplary treatment devices may include a linear accelerator, an X-ray treatment device, etc. The couch 116 may be configured to support and/or transfer the at least one part of the subject to for example, a scanning region of the imaging device 112 and/or the treatment device 114. For example, the couch 116 may be moved to transfer the subject from the imaging device 112 to the treatment device 114.

In some embodiments, the IGRT apparatus 110 may include two gantries that house the imaging device 112 and the treatment device 114, respectively. The imaging device 112 and the corresponding gantry may be spaced by a distance from the treatment device 114 and the corresponding gantry. In some embodiments, the corresponding gantry of the imaging device 112 and the corresponding gantry of the treatment device 114 may have collinear bores. For example, a bore of the gantry of the imaging device 112 and a bore of the gantry of the treatment device 114 may share an axis of rotation. The subject may be positioned in different positions in the table 116 for imaging and treatment. In some embodiments, the imaging radiation source of the imaging device 112 and the treatment radiation source of the treatment device 114 may be integrated as one radiation source to imaging and/or treat the subject. Merely by way of example, the IGRT apparatus 110 may include a treatment device and a CT scanner. Descriptions of such a device may be found in, e.g., US Publication Nos. 20170189720A1 and 20170189724A1, both entitled "Radiation therapy system," and US Publication No. 20170189719A1 entitled "Radiation therapy positioning system," the contents of each of which are hereby incorporated by reference.

The processing device 120 may process data and/or information obtained from the IGRT apparatus 110, the storage 130, and/or the terminal(s) 140. For example, the processing device 120 may reconstruct an image relating to at least one part of a subject (e.g., a tumor) based on projection data collected by the IGRT apparatus 110 (e.g., the imaging device 112). As another example, the processing device 120 may determine one or more neural network models for denoising configured to process and/or convert image data. As a further example, the processing device 120 may determine a treatment plan based on at least one part of the subject (e.g., a tumor) represented in an image acquired by the imaging device 112.

In some embodiments, the processing device 120 may be a single server or a server group. The server group may be centralized or distributed. In some embodiments, the processing device 120 may be local or remote. For example, the processing device 120 may access information and/or data from the IGRT apparatus 110, the storage 130, and/or the terminal(s) 140 via the network 150. As another example, the processing device 120 may be directly connected to the IGRT apparatus 110, the terminal(s) 140, and/or the storage 130 to access information and/or data. In some embodiments, the processing device 120 may be implemented on a cloud platform. For example, the cloud platform may include a private cloud, a public cloud, a hybrid cloud, a community cloud, a distributed cloud, an inter-cloud, a multi-cloud, or the like, or a combination thereof. In some embodiments, the processing device 120 may be implemented by a mobile device 300 having one or more components as described in connection with FIG. 3.

The storage 130 may store data, instructions, and/or any other information. In some embodiments, the storage 130 may store data obtained from the IGRT apparatus 110, the processing device 120, and/or the terminal(s) 140. In some embodiments, the storage 130 may store data and/or instructions that the processing device 120 may execute or use to perform exemplary methods described in the present disclosure. In some embodiments, the storage 130 may include a mass storage, a removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 130 may be implemented on a cloud platform as described elsewhere in the disclosure.

In some embodiments, the storage 130 may be connected to the network 150 to communicate with one or more other components in the diagnostic and treatment system 100 (e.g., the processing device 120, the terminal(s) 140, etc.). One or more components in the diagnostic and treatment system 100 may access the data or instructions stored in the storage 130 via the network 150. In some embodiments, the storage 130 may be part of the processing device 120.

The terminal(s) 140 may be connected to and/or communicate with the IGRT apparatus 110, the processing device 120, and/or the storage 130. For example, the terminal(s) 140 may obtain a processed image from the processing device 120. As another example, the terminal(s) 140 may obtain image data acquired via the IGRT apparatus 110 and transmit the image data to the processing device 120 to be processed. In some embodiments, the terminal(s) 140 may include a mobile device 140-1, a tablet computer 140-2, . . . , a laptop computer 140-N, or the like, or any combination thereof. For example, the mobile device 140-1 may include a mobile phone, a personal digital assistance (PDA), a gaming device, a navigation device, a point of sale (POS) device, a laptop, a tablet computer, a desktop, or the like, or any combination thereof. In some embodiments, the terminal(s) 140 may include an input device, an output device, etc. The input device may include alphanumeric and other keys that may be input via a keyboard, a touch screen (for example, with haptics or tactile feedback), a speech input, an eye tracking input, a brain monitoring system, or any other comparable input mechanism. The input information received through the input device may be transmitted to the processing device 120 via, for example, a bus, for further processing. Other types of the input device may include a cursor control device, such as a mouse, a trackball, or cursor direction keys, etc. The output device may include a display, a speaker, a printer, or the like, or a combination thereof. In some embodiments, the terminal(s) 140 may be part of the processing device 120.

The network 150 may include any suitable network that can facilitate exchange of information and/or data for the diagnostic and treatment system 100. In some embodiments, one or more components of the diagnostic and treatment system 100 (e.g., the IGRT apparatus 110, the processing device 120, the storage 130, the terminal(s) 140, etc.) may communicate information and/or data with one or more other components of the diagnostic and treatment system 100 via the network 150. For example, the processing device 120 may obtain image data from the IGRT apparatus 110 via the network 150. As another example, the processing device 120 may obtain user instruction(s) from the terminal(s) 140 via the network 150. The network 150 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network (VPN), a satellite network, a telephone network, routers, hubs, witches, server computers, and/or any combination thereof. For example, the network 150 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 150 may include one or more network access points. For example, the network 150 may include wired and/or wireless network access points such as base stations and/or internet exchange points through which one or more components of the diagnostic and treatment system 100 may be connected to the network 150 to exchange data and/or information.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the storage 130 may be a data storage including cloud computing platforms, such as, public cloud, private cloud, community, and hybrid clouds, etc. As another example, the diagnostic and treatment system 100 may further include a treatment planning system. However, those variations and modifications do not depart the scope of the present disclosure.

FIG. 2 is a schematic diagram illustrating exemplary hardware and/or software components of an exemplary computing device 200 on which the processing device 120 may be implemented according to some embodiments of the present disclosure. As illustrated in FIG. 2, the computing device 200 may include a processor 210, storage 220, an input/output (I/O) 230, and a communication port 240.

The processor 210 may execute computer instructions (e.g., program code) and perform functions of the processing device 120 in accordance with techniques described herein. The computer instructions may include, for example, routines, programs, objects, components, data structures, procedures, modules, and functions, which perform particular functions described herein. For example, the processor 210 may process image data obtained from the IGRT device 110, the storage 130, terminal(s) 140, and/or any other component of the diagnostic and treatment system 100. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or a combinations thereof.

Merely for illustration, only one processor is described in the computing device 200. However, it should be noted that the computing device 200 in the present disclosure may also include multiple processors. Thus operations and/or method steps that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage 220 may store data/information obtained from the IGRT device 110, the storage 130, the terminal(s) 140, and/or any other component of the diagnostic and treatment system 100. In some embodiments, the storage 220 may include a mass storage, removable storage, a volatile read-and-write memory, a read-only memory (ROM), or the like, or a combination thereof. For example, the mass storage may include a magnetic disk, an optical disk, a solid-state drive, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure. For example, the storage 220 may store a program for the processing device 120 for determining a target flip angle schedule.

The I/O 230 may input and/or output signals, data, information, etc. In some embodiments, the I/O 230 may enable a user interaction with the processing device 120. In some embodiments, the I/O 230 may include an input device and an output device. Examples of the input device may include a keyboard, a mouse, a touch screen, a microphone, or the like, or a combination thereof. Examples of the output device may include a display device, a loudspeaker, a printer, a projector, or the like, or a combination thereof. Examples of the display device may include a liquid crystal display (LCD), a light-emitting diode (LED)-based display, a flat panel display, a curved screen, a television device, a cathode ray tube (CRT), a touch screen, or the like, or a combination thereof.

The communication port 240 may be connected to a network (e.g., the network 150) to facilitate data communications. The communication port 240 may establish connections between the processing device 120 and the IGRT apparatus 110, the storage 130, and/or the terminal(s) 140. The connection may be a wired connection, a wireless connection, any other communication connection that can enable data transmission and/or reception, and/or a combination of these connections. The wired connection may include, for example, an electrical cable, an optical cable, a telephone wire, or the like, or a combination thereof. The wireless connection may include, for example, a Bluetooth™ link, a Wi-Fi™ link, a WiMax™ link, a WLAN link, a ZigBee link, a mobile network link (e.g., 3G, 4G, 5G, etc.), or the like, or a combination thereof. In some embodiments, the communication port 240 may be and/or include a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
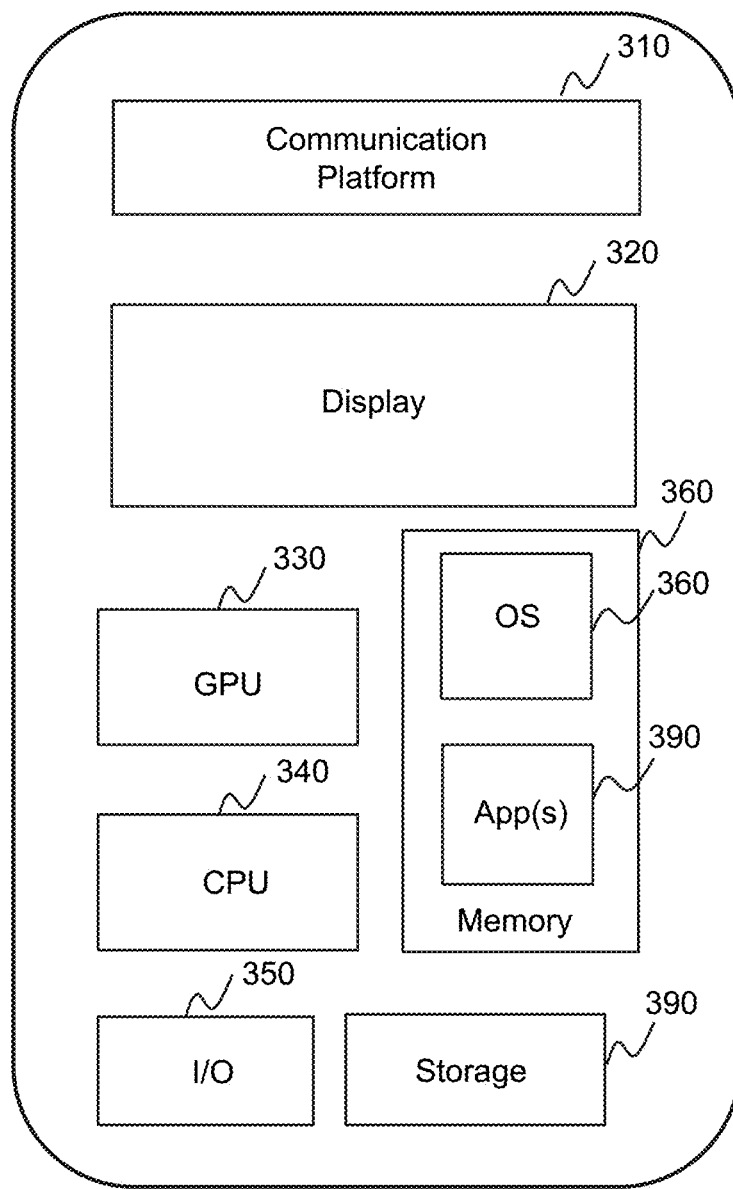
FIG. 3 is a schematic diagram illustrating exemplary hardware and/or software components of an exemplary mobile device on which the terminal(s) may be implemented according to some embodiments of the present disclosure.

FIG. 3 is a schematic diagram illustrating exemplary hardware and/or software components of an exemplary mobile device 300 on which the terminal(s) 140 may be implemented according to some embodiments of the present disclosure. As illustrated in FIG. 3, the mobile device 300 may include a communication platform 410, a display 320, a graphic processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS™, Android™, Windows Phone™, etc.) and one or more applications 380 may be loaded into the memory 360 from the storage 390 in order to be executed by the CPU 340. The applications 380 may include a browser or any other suitable mobile apps for receiving and rendering information relating to image processing or other information from the processing device 120. User interactions with the information stream may be achieved via the I/O 350 and provided to the processing device 120 and/or other components of the diagnostic and treatment system 100 via the network 150.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 4:
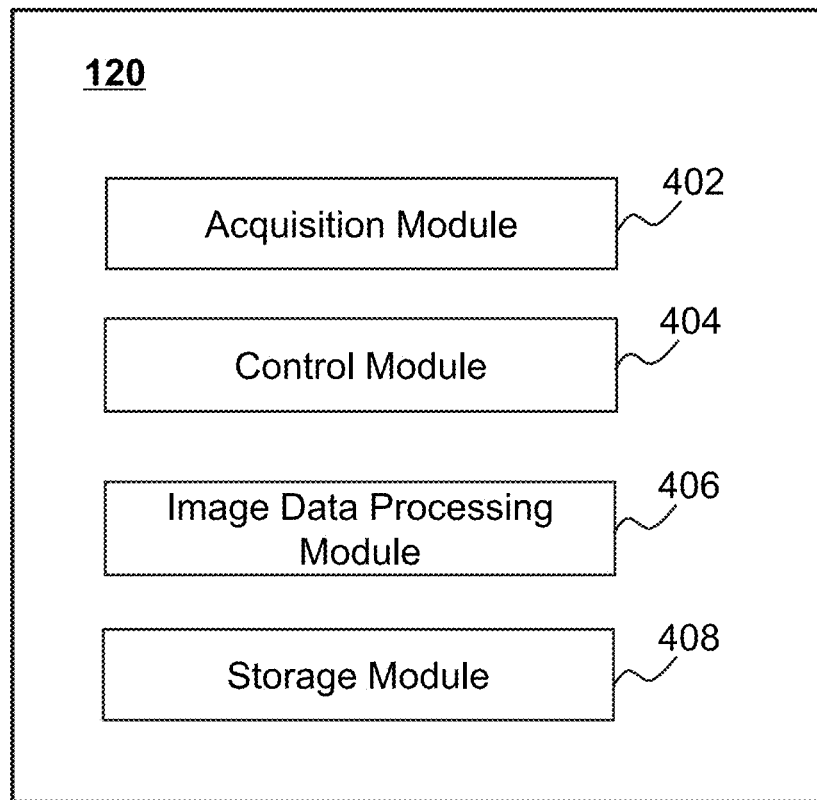
FIG. 4 is a block diagram illustrating an exemplary processing device according to some embodiments of the present disclosure.

FIG. 4 is a block diagram illustrating an exemplary processing device 120 according to some embodiments of the present disclosure. The processing device 120 may include an acquisition module 402, a control module 404, an image data processing module 406, and a storage module 408. At least a portion of the processing device 120 may be implemented on a computing device as illustrated in FIG. 2 or a mobile device as illustrated in FIG. 3.

The acquisition module 402 may acquire data. In some embodiments, the data may be acquired from the IGRT apparatus 110, the storage 130, and/or the terminal(s) 140. In some embodiments, the data may include image data (e.g., a radiological image, projection data, etc.), models, instructions, or the like, or a combination thereof. The models may be used to generate an image. The instructions may be executed by the processor(s) of the processing device 120 to perform exemplary methods described in the present disclosure. In some embodiments, the acquired data may be transmitted to the image data processing module 406 for further processing, or stored in the storage module 408.

The control module 404 may control operations of the acquisition module 402, the image data processing module 406, and/or the storage module 408, for example, by generating one or more control parameters. For example, the control module 404 may control the acquisition module 402 to acquire image data (e.g., an image, projection data, etc.) from the imaging device 112 of the IGRT apparatus 110. As another example, the control module 404 may control the image data processing module 406 to generate an image relating to a subject. As a further example, the control module 404 may control the image data processing module 406 to determine a radiotherapy treatment of the subject based on the image. In some embodiments, the control module 404 may receive a real-time command or retrieve a predetermined instruction provided by a user (e.g., a doctor) to control one or more operations of the acquisition module 402 and/or the image data processing module 406. For example, the control module 404 may adjust the acquisition module 402 and/or the image data processing module 406 to generate image data (e.g., an image) according to the real-time instruction and/or the predetermined instruction. In some embodiments, the control module 404 may communicate with one or more other modules of the processing device 120 for exchanging information and/or data.

The image data processing module 406 may process data provided by various modules of the processing device 120. In some embodiments, the image data processing module 406 may generate high-dose image data based on low-dose image data. For example, the image data processing module 406 may generate high-dose image data using a neural network model for denoising. As another example, the image data processing module 406 may generate high-dose image data using an iterative reconstruction technique based on a statistical model of noises. In some embodiments, the image data processing module 406 may determine a radiotherapy treatment based on the high-dose image data.

The storage module 408 may store information. The information may include programs, software, algorithms, data, text, number, images and some other information. For example, the information may include image data (e.g., a radiological image, an optical image, etc.), motion or position data (e.g., a speed, a displacement, an acceleration, a spatial position, etc.) relating to a component in the IGRT apparatus 110 (e.g., the couch 116), instructions, or the like, or a combination thereof. In some embodiments, the storage module 408 may store program(s) and/or instruction(s) that can be executed by the processor(s) of the processing device 120 to acquire data, determine a spatial position of at least one part of a subject.

Figure 5:
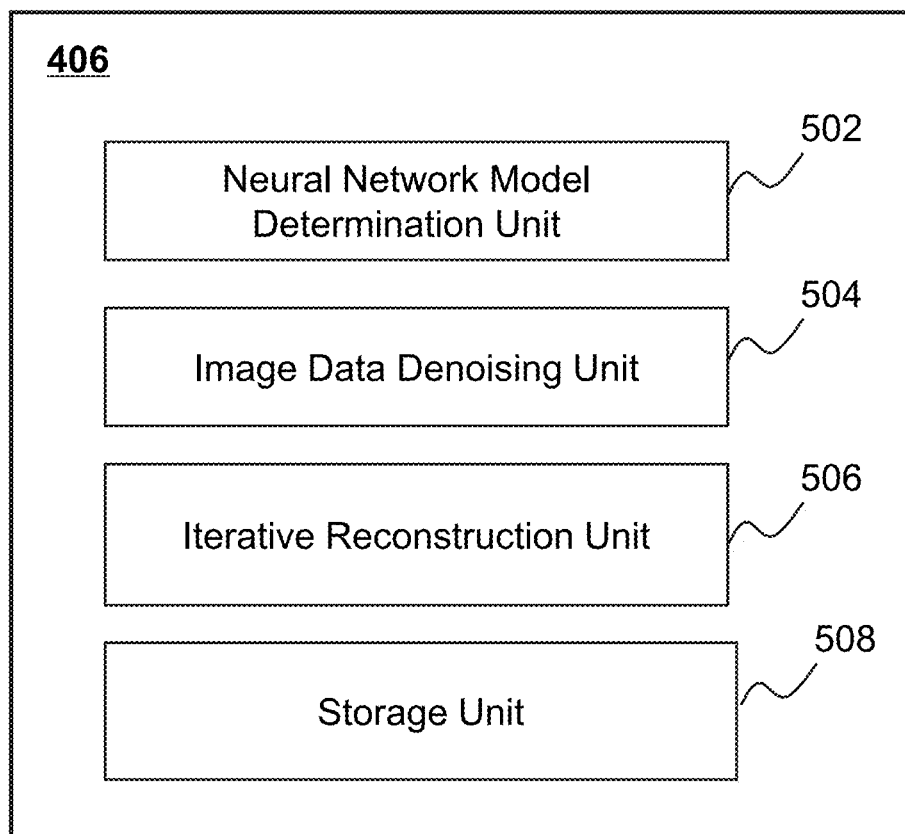
FIG. 5 is a block diagram illustrating an exemplary image data processing module according to some embodiments of the present disclosure.

In some embodiments, one or more modules illustrated in FIG. 5 may be implemented in at least part of the diagnostic and treatment system 100 as illustrated in FIG. 1. For example, the acquisition module 402, the control module 404, the image data processing module 406, and/or the storage module 408 may be integrated into a console (not shown). Via the console, a user may set parameters for scanning a subject, controlling imaging processes, controlling parameters for reconstruction of an image, etc. In some embodiments, the console may be implemented via the processing device 120 and/or the terminal(s) 140.

FIG. 5 is a block diagram illustrating an exemplary image data processing module 406 according to some embodiments of the present disclosure. The image data processing module 406 may include a neural network model determination unit 502, an image denoising unit 504, an iterative reconstruction unit 506, and a storage unit 508. At least a portion of the image data processing module 406 may be implemented on a computing device as illustrated in FIG. 2 or a mobile device as illustrated in FIG. 3.

The neural network model determination unit 502 may be configured to generate a neural network model for denoising. In some embodiments, the neural network model determination unit 502 may generate a general network model for denoising via training a neural network model based on multiple groups of training data relating to multiple different subjects. In some embodiments, the neural network model determination unit 502 may train the general neural network model for denoising based on training data relating to a specified subject to obtain a personalized neural network model for denoising.

In some embodiments, the neural network model determination unit 502 may transmit the neural network model for denoising to other units or blocks of the image data processing module 406 for further processing. For example, the neural network model determination unit 502 may transmit the neural network model for denoising to the image data denoising unit 504 for processing image data. As another example, the neural network model determination unit 502 may transmit the neural network model for denoising to the storage unit 508 for storage.

The image data denoising unit 504 may be configured to denoise image data. For example, the image data denoising unit 504 may convert low-dose image data to high-dose image data using a neural network model for denoising determined by, for example, the neural network model determination unit 502. As another example, the image data denoising unit 504 may determine noise data included in low-dose image data using a neural network model for denoising, and determine high-dose image data corresponding to the low-dose image data based on the noise data and the low-dose image data.

The iterative reconstruction unit 506 may be configured to generate a high-dose image based on corresponding low-dose projection data and a statistical model of noises by performing a plurality of iterations. In some embodiments, the iterative reconstruction unit 506 may generate the statistical model of noises relating to the low-dose projection data. In some embodiments, the iterative reconstruction unit 506 may denoise the low-dose projection data based on the statistical model of noises, and reconstruct an image based on the denoised low-dose projection data. In some embodiments, the iterative reconstruction unit 506 may denoise the image based on the statistical model of noises to obtain the high-dose image corresponding to the low-dose projection data.

The storage unit 508 may store information relating to, for example, training a neural network model, a statistical model of noises, etc. The information may include programs, software, algorithms, data, text, number, and some other information. In some embodiments, the information relating to training a neural network model may include images for training a neural network model, algorithms for training a neural network model, parameters of a neural network model, etc. The storage unit 580 may be a memory that stores data to be processed by processing devices, such as CPUs, GPUs, etc. In some embodiments, the storage unit 508 may be a memory that may be accessible by one or more GPUs, or may be memory that is only accessible by a specific GPU.

It should be noted that the above description of the processing module 430 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, the neural network model determination unit 502 and the image data denoising unit 504 may be integrated into one single unit.

Figure 6:
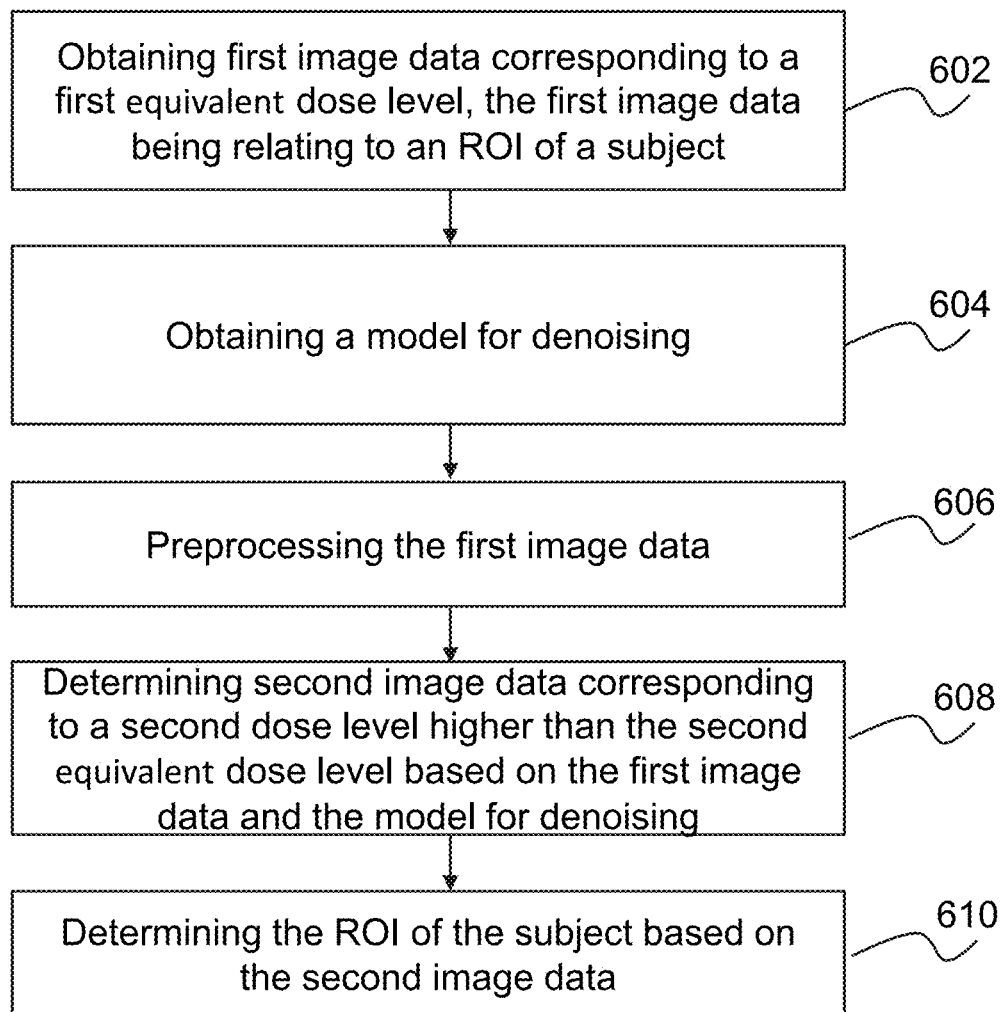
FIG. 6 is a flowchart illustrating an exemplary process for processing image data according to some embodiments of the present disclosure.

FIG. 6 is a flowchart illustrating an exemplary process 600 for processing image data according to some embodiments of the present disclosure. In some embodiments, one or more operations of process 600 illustrated in FIG. 6 may be implemented in the diagnostic and treatment system 100 illustrated in FIG. 1. For example, the process 600 illustrated in FIG. 6 may be stored in the storage 130 in the form of instructions, and invoked and/or executed by the processing device 120 (e.g., the processor 210 of the computing device 200 as illustrated in FIG. 2, the GPU 330 or CPU 340 of the mobile device 300 as illustrated in FIG. 3).

In 602, first image data corresponding to a first equivalent dose level and relating to the ROI of the subject may be obtained. Operation 602 may be performed by the acquisition module 402. The term "equivalent dose level" may also refer to the radiation energy of radiation received by a unit mass of a subject in a scanning procedure when simulating different numbers of photons. In some embodiments, the equivalent dose level may equal to a scanning dose level relating to the subject. In some embodiments, the first image data may obtained from the storage 130, the storage module 408, or any other external storage. In some embodiments, the first image data may be obtained from an imaging device of an IGRT apparatus (e.g., the imaging device 112 of the IGRT apparatus 110) generated by scanning the subject at the first equivalent dose level. The first image data may include projection data, an image relating to the ROI of the subject, or the like, or a combination thereof. The first image data may include two-dimensional (2D) image data, three-dimensional (3D) image data, four-dimensional (4D) image data, or image data of other dimensions.

In some embodiments, the first image data may include planning image data (e.g., a planning image, planning projection data, etc.) relating to the ROI of the subject. As used herein, planning image data may be used to design a treatment plan of the subject. For example, before the subject receives a radiation therapy (e.g., days or weeks before), planning image may be taken. The planning image may be used to identify a radiotherapy target (e.g., the ROI of the subject), an organ at risk, and the external contour (e.g., skin) of the subject, and the treatment plan may be designed for the subject based on the planning image. In some embodiments, the first image data may include guiding image data (e.g., a guiding image, guiding projection data, etc.) relating to the ROI of the subject. As used herein, guiding image data may be used to guide the implementation of the treatment plan. For example, the guiding image relating to the ROI of the subject may be used to position the ROI. The positioned ROI may receive radiation according to the treatment plan. The guiding image data may be taken during or before the radiation therapy (e.g., on the day of treatment, or hours before the treatment, or minutes before the treatment, or seconds before the treatment, or during the treatment). In some embodiments, the treatment plan may be delivered to the subject during several treatment fractions spread over a treatment period of multiple days. During the treatment period, one or more guiding images (e.g., a CT image) may be used to determine and/or position the ROI (e.g., a cancer) of the subject during the several treatment fractions.

The first equivalent dose level of the first image data may satisfy a first condition. In some embodiments, the first condition may include a first threshold or a first range. For example, the first equivalent dose level may be equal to or lower than the first threshold. As another example, the first equivalent dose level may be in the first range. In some embodiments, the first condition (e.g., the first threshold or the first range) may vary according to clinical demands (e.g., a type of a tissue of interest). For example, in a liver scan, the first equivalent dose level may be equal to or lower than 15 mSv, or 10 mSv, or 5 mSv, etc. As another example, in a chest scan, the first equivalent dose level may be equal to or lower than 7 mSv, or 2 mSv, etc. As still an example, in an epigastrium scan with a CBCT device, the first equivalent dose level may be equal to 4 mGy. In an epigastrium scan with a CT device under scanning parameters 120 kv and 30 mAs, the first equivalent dose level may be equal to 1.5 mGy.

In 604, a model for denoising may be obtained. Operation 604 may be performed by the acquisition module 402. In some embodiments, the model for denoising may be pre-determined (e.g., provided by a manufacturer of an IGRT apparatus, an entity specializing in image processing, an entity having access to training data, etc.). In some embodiments, the model for denoising may be obtained from the storage 130, the storage module 408, the storage unit 508, the terminal(s) 140, or other storage devices.

In some embodiments, the model for denoising may include a neural network model for denoising. The neural network model for denoising may be configured to process image data (e.g., the first image data obtained in 602). Exemplary image data processing may include transform, modification, and/or conversion, etc. For example, the neural network model for denoising may be configured to convert low-dose image data (e.g., the first image data obtained in 602) to high-dose image data (e.g., the second image data determined in 608) corresponding to the low-dose image data. As another example, the neural network model for denoising may be configured to reduce the noise level in image data (e.g., the first image data obtained in 602). As still an example, the neural network model for denoising may extract noise data from image data (e.g., the first image data obtained in 602). In some embodiments, the neural network model for denoising may include a general neural network model for denoising generated based on training data acquired from multiple objects. In some embodiments, the neural network model for denoising may include a personalized neural network model corresponding to the subject. More descriptions of the neural network model for denoising may be found in FIG. 7 and FIG. 8 and the descriptions thereof.

In some embodiments, the model for denoising may include a statistical model of noises. The statistical model of noises may represent the noise level of image data (e.g., the first image data obtained in 602). In some embodiments, the statistical model of noises may be constructed based on a spatial-domain filter model, a transform-domain filter model, a morphological noise filter model, or the like, or a combination thereof. The spatial-domain filter model may include a field average filter model, a median filter model, a Gaussian filter model, or the like, or a combination thereof. The transform-domain filter model may include a Fourier transform model, a Walsh-Hadamard transform model, a cosine transform model, a K-L transform model, a wavelet transform model, or the like, or a combination thereof. In some embodiments, the statistical model of noises may include a partial differential model or a variational model, such as a Perona-Malik (P-M) model, a total variation (TV) model, or the like, or a combination thereof. In some embodiments, the statistical model of noises may include a noise estimation of the first image data. The noise estimation of the first projection data may represent the noise level of the first image data. In some embodiments, noises included in the first image data may include quantum noises incurred by radiation (e.g., X-rays), electronic noises incurred by a component of an imaging device (e.g., the detector in the imaging device 112), or the like, or a combination thereof. The noise estimation of the first image data may be determined based on the quantum noises, the electronic noises, and an intensity of radiation detected by a detector (e.g., the detector in the imaging device 112). More descriptions of the statistical model of noises may be found in, for example, Chinese Publication No 103971387B, entitled "SYSTEM AND METHOD FOR CT IMAGE RECONSTRUCTION," the contents of which are hereby incorporated by reference.

In 606, the first image data may be preprocessed. Operation 606 may be performed by the image data processing module 406. The preprocessing operation may be performed to adjust the quality of image data, such as the noise level of image data, the contrast ratio of an image, etc. In some embodiments, the preprocessing operation may include a denoising operation, an enhancement operation, a smoothing operation, an image fusion operation, an image segmentation operation, an image registration operation, or the like, or a combination thereof. Specifically, the smoothing operation may be performed based on a Gaussian filter, an average filter, a median filter, a wavelet transformation, or the like, or a combination thereof. The enhancing operation may include a histogram equalization, an image sharpening, a Fourier transform, a high-pass filtering, a low-pass filtering, or the like, or a combination thereof. The denoising operation may include applying a spatial-domain filter, a transform-domain filter, a morphological noise filter, or the like, or a combination thereof. The image segmentation operation may be performed based on a segmentation algorithm. Exemplary segmentation algorithms may include a threshold-based segmentation algorithm, an edge-based segmentation algorithm, a region-based segmentation algorithm, or the like, or a combination thereof. The image fusion operation may be performed using, for example, an optimal seam-line algorithm, a gradient pyramid algorithm, etc. The image registration operation may be performed using, for example, a cross-correlation algorithm, a Walsh transform algorithm, a phase correlation algorithm, etc.

In 608, second image data corresponding to a second equivalent dose level higher than the first equivalent dose level may be determined based on the first image data and the model for denoising. Operation 608 may be performed by the image data processing module 406. In some embodiments, the second image data may include projection data, an image, or the like, or a combination thereof. The second equivalent dose level may be an equivalent dose level of the first image data relative to the first equivalent dose level. As used herein, the second equivalent dose level may refer to a dose level required by the first image data when the noise level of the first image data is equal to that of the second image data. The equivalent dose level may also refer to the radiation energy of radiation received by a unit mass of a subject in a scanning procedure when simulating different numbers of photons. A ratio of the first equivalent dose level to the second equivalent dose level may be equal to or exceed 10%, or 15%, or 25%, or 30%, or 40%, or 50%, 85%, etc. In an epigastrium scan, a ratio of the first equivalent dose level to the second equivalent dose level may range from equal to or exceed 10%, or 15%, or 25%, or 30%, or 40%, or 50%, 85%, etc. For example, for a CBCT scan, the ratio of the first equivalent dose level to the second equivalent dose level may equals to or exceeds 1:3, or 1:2. For a CT scan, the ratio of the first equivalent dose level to the second equivalent dose level may equal to 1:7, or 1:5.

Figure 8:
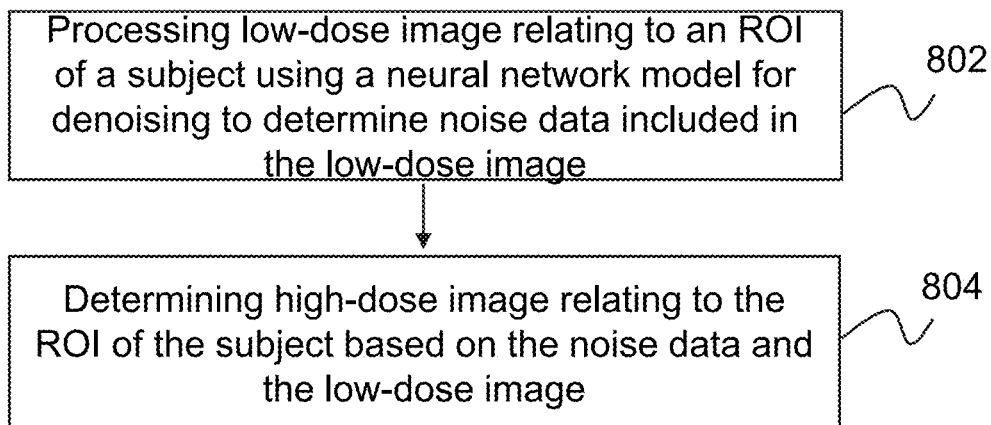
FIG. 8 is a flowchart illustrating an exemplary process for determining a neural network model for denoising according to some embodiments of the present disclosure.

The second image data may be determined based on the model for denoising obtained in 604. For example, the second image data may be determined based on the neural network model for denoising. Further, the second image data may be determined via converting the first image data into the second image data directly using the neural network model for denoising. As another example, the first image data may be converted into noise data using the neural network model for denoising. Then, the second image data may be determined based on the noise data and the first image data according to process 800 as illustrated in FIG. 8. As another example, the second image data may be determined based on the statistical model of noises using an iterative reconstruction technique. For example, the first image data may include first projection data. The second image data may include a second image. The second image may be reconstructed by performing a plurality of iterations based on an objective function including the statistical model of noises obtained in 604. As still an example, the first projection data may be denoised based on the statistical model of noises in a projection domain obtained in 604. The second image may be generated based on the denoised first projection data. The second image may be denoised based on the statistical model of noises in an image domain. More descriptions of determining the second image data based on the statistical model of noises may be found in FIGS. 9, 10, and/or 11 and the descriptions thereof.

In 610, the ROI of the subject may be determined based on the second image data. Operation 610 may be performed by the image data image data processing module 406. In some embodiments, the determination of the ROI of the subject may include identifying the ROI or tissues around the ROI, drawing the outline of the ROI, obtaining information relating to the ROI, etc. In some embodiments, a treatment plan of the subject may be determined based on the determined information relating to the ROI of the subject. In some embodiments, the information relating to the ROI may be recorded for further processing. For example, the information relating to the ROI determined based on the second image data may be compared with information relating to the ROI acquired from a predetermined treatment plan of the subject. Then, a position of the first subject in space may be adjusted based on the comparison, for example, via moving or rotating a couch of an IGRT apparatus (e.g., the couch 116), such that radiation of a certain dose may be delivered to the subject or the ROI of the subject according to a predetermined treatment plan of the subject. In some embodiments, the predetermined treatment plan of the subject may be modified based on the comparison. In some embodiments, when during or after a treatment, a delivery of treatment radiation beam may be performed based on the comparison. For example, if the comparison is outside a range, a delivery of treatment radiation beam may be deactivated. If the comparison is within a range, a delivery of treatment radiation beam may be reactivated.

In some embodiments, the predetermined treatment plan of the first subject may be obtained from the storage 130, the terminal(s) 140, the storage module 408, or any other external storage. In some embodiments, the predetermined treatment plan of the subject may be determined by, for example, the diagnostic and treatment system 100 or other systems (e.g., a treatment planning system (TPS) connected to the diagnostic and treatment system 100).

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, operation 606 may be omitted. As another example, in 608, the second image data may be determined based on the preprocessed first image data determined in 606. In some embodiments, process 600 may further include determining or adjusting a treatment plan based on the determined ROI in 610. In some embodiments, process 600 may further include adjust a position of the subject based on the determined ROI in 610.

Figure 7:
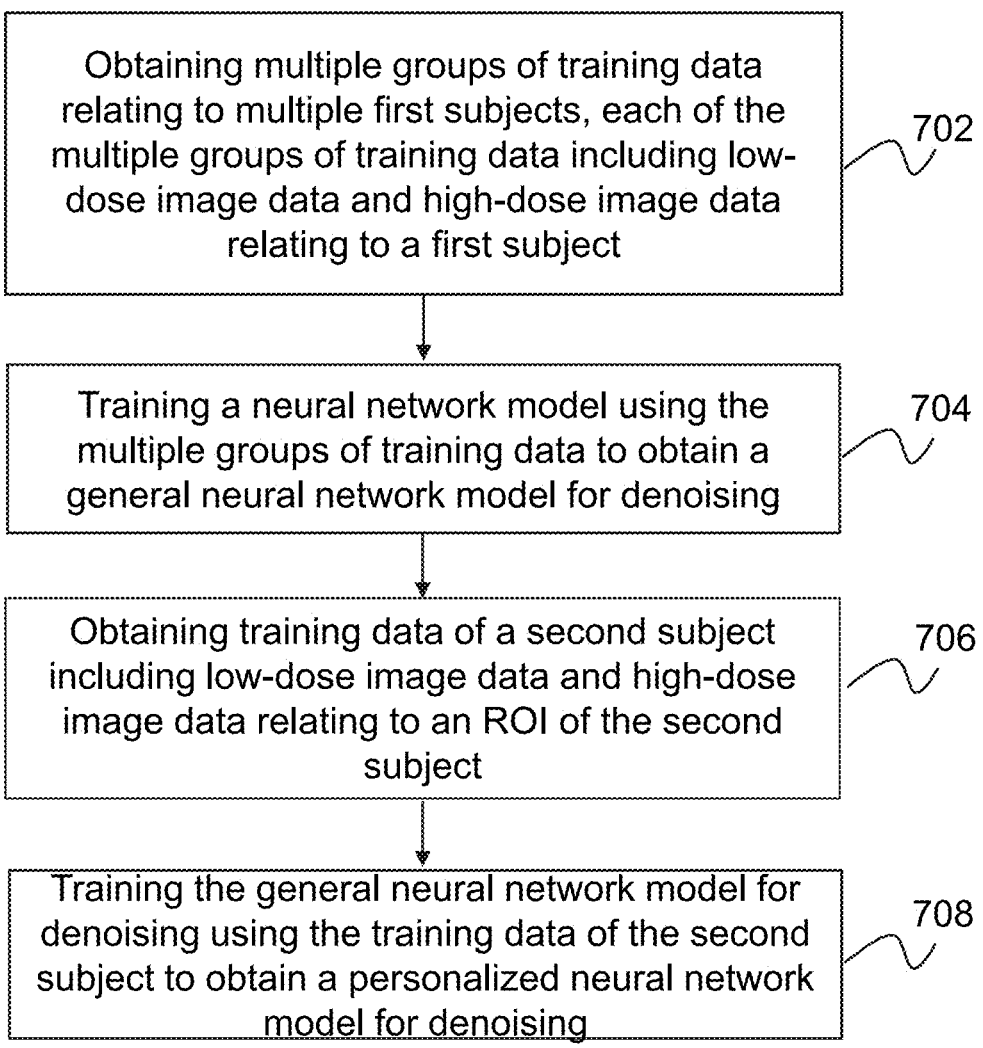
FIG. 7 is a flowchart illustrating an exemplary process for processing low-dose image data based on a neural network model for denoising according to some embodiments of the present disclosure.

FIG. 7 is a flowchart illustrating an exemplary process 700 for determining a neural network model for denoising according to some embodiments of the present disclosure. In some embodiments, one or more operations of process 700 illustrated in FIG. 7 may be implemented in the diagnostic and treatment system 100 illustrated in FIG. 1. For example, the process 700 illustrated in FIG. 7 may be stored in the storage 130 in the form of instructions, and invoked and/or executed by the processing device 120 (e.g., the processor 210 of the computing device 200 as illustrated in FIG. 2, the GPU 330 or CPU 340 of the mobile device 300 as illustrated in FIG. 3). The model for denoising mentioned in operation 604 may be determined according to process 700.

In 702, multiple groups of training data relating to multiple first subjects may be obtained, each of the multiple groups of training data including low-dose image data and high-dose image data relating to a first subject. Operation 702 may be performed by the acquisition module 402. The multiple groups of training data relating to multiple ROIs of the multiple first subjects may be obtained from the IGRT apparatus 110, the storage 130, the terminal(s) 140, the storage module 408, the storage unit 508, and/or other external storages. The high-dose image data may include high-dose projection data or a high-dose image corresponding to a first equivalent dose level. The low-dose image data may include low-dose projection data or low-dose image corresponding to a second equivalent dose level lower than the first equivalent dose level. In some embodiments, the first equivalent dose level and the second equivalent dose level may vary according to clinical demands (e.g., a type of a tissue). For example, in a liver scan, the first equivalent dose level may be equal to or exceed 5 mSv, or 10 mSv, or 15 mSv, etc. The second equivalent dose level may be lower than 15 mSv, or 10 mSv, or 5 mSv, etc. A ratio of the second equivalent dose level to the first equivalent dose level may range from 5% to 40%, such as 10%, 15%, 20%, 25%, 30%, etc. As another example, in a chest scan, the first equivalent dose level may be equal to or exceed 2 mSv, or 7 mSv, etc. The second equivalent dose level may be lower than 7 mSv, or 2 mSv, etc. In some embodiments, a ratio of the first equivalent dose level to an estimated effective dose may be equal to or exceed 1%, or 5%, or 10%, or 25%, or 50%, or 100%, or 150%, etc. A ratio of the second equivalent dose level to the estimated effective dose may be equal to or below 1%, or 5%, or 10%, or 25%, etc.

In some embodiments, both the high-dose image data and the corresponding low-dose image data may be obtained from an imaging device (e.g., the imaging device 112 of the IGRT apparatus 110) generated by scanning one of the multiple first subjects being examined. As used herein, the corresponding high-dose image data and the low-dose image data may refer to a representation of a same portion of the first subject (e.g., an ROI of the second subject). In some embodiments, the low-dose image data corresponding to the high-dose image data may be determined based on the high-dose image data. For example, the low-dose image data may include low-dose projection data. The high-dose image data may include high-dose projection data. The low-dose projection data may be determined by way of simulation based on the high-dose projection data. More descriptions of determining the low-dose image data based on the corresponding high-dose image data may be found in, for example, International Application No PCT/CN2017/095071, entitled "SYSTEM AND METHOD FOR IMAGE CONVERSION," filed Jul. 28, 2017, the contents of which are hereby incorporated by reference.

In 704, a neural network model may be trained using the multiple groups of training data to obtain a general neural network model for denoising. Operation 704 may be performed by the neural network model determination unit 502. In some embodiments, the neural network model may be pre-determined (e.g., provided by a manufacturer of an IGRT apparatus, an entity specializing in image processing, an entity having access to training data, etc.). In some embodiments, the neural network model may be obtained from the storage 130, the storage module 408, the storage unit 508, the terminal(s) 140, or other storages. In some embodiments, the neural network model may be constructed based on a back propagation (BP) neural network, a convolutional neural network (CNN), a recurrent neural network (RNN), a long short-term memory (LSTM), a generative adversarial network (GAN), an adaptive resonance theory (ART) neural network, or the like, or a combination thereof. In some embodiments, the neural network model may be constructed as a two-dimensional (2D) model, a three-dimensional (3D) model, a four-dimensional (4D) model, or a model of any other dimensions. See, for example, FIG. 12 and the description thereof. In some embodiments, the neural network model may be trained by inputting each group of the multiple groups of training data using a machine training algorithm. Exemplary machine training algorithms may include a gradient descent algorithm, a Newton algorithm, a conjugate gradient algorithm, a Quasi-Newton algorithm, a Levenberg-Marguardt algorithm, or the like, or a combination thereof. More descriptions of the general neural network model for denoising may be found in, for example, International Application No. PCT/CN2017/095071, entitled "SYSTEM AND METHOD FOR IMAGE CONVERSION," filed Jul. 28, 2017, the contents of which are hereby incorporated by reference.

In some embodiments, multiple pairs of image blocks may be extracted from each group of the training data relating to multiple first subjects. As used herein, each pair of the multiple pairs of image blocks may include an image block extracted from the high-dose image data and an image block extracted from the low-dose image data relating to one of the multiple first subjects. A pair of image blocks may correspond to the same region in the ROI of one of the multiple first subjects. In some embodiments, the multiple first subjects may include a specific subject (e.g., the second subject as described in 706). The multiple groups of training data relating to the multiple first subjects may include a group of training data relating to the specific subject (e.g., the second subject as described in 706). Further, multiple pairs of image blocks relating to the specific subject (e.g., the second subject described in 706) may be extracted from the group of training data relating to the specific subject (e.g., the second subject as described in 706). The neural network model may be trained iteratively. In each iteration, at least one portion of multiple pairs of image blocks relating to multiple second subjects including multiple pairs of image blocks relating to the specified subject (e.g., the second subject described in 706) may be selected based on, for example, a stochastic gradient descent algorithm, to train the neural network model. Parameters (e.g., weight value) of the neural network may be adjusted in each iteration until, for example, all the multiple pairs of image blocks may be used to train the neural network model, or a certain number of iterations are performed.

In 706, training data of a second subject including low-dose image data and high-dose image data relating to an ROI of the second subject may be obtained. Operation 706 may be performed by the acquisition module 402. In some embodiments, the training data of the second subject may include high-dose image data and corresponding low-dose image data. As used herein, the corresponding high-dose image data and the low-dose image data may refer to a representation of a same portion of the second subject (e.g., the ROI of the second subject). In some embodiments, the high-dose image data may be acquired by a first device. The low-dose image data may be acquired by a second device. The first device may be same as or different from the second device. For example, the first device may include an imaging device, such as a CT device. The second device may include an imaging device of an IGRT apparatus (e.g., the imaging device 112 of the IGRT apparatus 110). In some embodiments, the multiple first subjects may include the second subject. Further, the multiple groups of the training data relating to the multiple first subjects may include the training data of the second subject.

In some embodiments, the high-dose image data may be used to determine a treatment plan of the second subject. For example, the high-dose image data may include planning image data (e.g., a planning image). In some embodiments, the high-dose image data may be used to guide the implementation of a predetermined treatment plan of the second subject. For example, the high-dose image data may include guiding image data (e.g., a guiding image) relating to the ROI of the second subject as described in connection with FIG. 6. In some embodiments, the high-dose image data may include fused image data (e.g., a fused image) relating to the ROI of the subject. For example, the fused image relating to the ROI of the second subject may be generated by fusing at least two of the guiding images relating to the ROI of the second subject acquired during a treatment period of the second subject. As another example, the fused image relating to the ROI of the second subject may be generated by fusing the planning image and one of the guiding images. In some embodiments, the high-dose image data may include a registration image relating to the ROI of the second subject. For example, the high-dose image data may include a CT-MRI registration image, a CT-PET registration image, etc.

The high-dose image data may correspond to a third equivalent dose level. The low-dose image data may correspond to a fourth equivalent dose level. The third equivalent dose level may be higher than the fourth equivalent dose level. In some embodiments, the third equivalent dose level and/or the fourth equivalent dose level may vary according to clinical demands (e.g., the type of a tissue). For example, in a liver scan, the third equivalent dose level may be equal to or exceed 5 mSv, or 10 mSv, or 15 mSv, etc. The fourth equivalent dose level may be lower than 15 mSv, or 10 mSv, or 5 mSv, etc. As another example, in a chest scan, the third equivalent dose level may be equal to or exceed 2 mSv, or 7 mSv, etc. The fourth equivalent dose level may be lower than 7 mSv, or 2 mSv, etc. As still an example, in an epigastrium scan with a CBCT device, the fourth equivalent dose level may be equal to 4 mGy. In an epigastrium scan with a CT device under scanning parameters 120 kv and 30 mAs, the fourth equivalent dose level may be equal to 1.5 mGy. In an epigastrium scan with a CT device under scanning parameters 120 kv and 220 mAs, the third equivalent dose level may be equal to 14 mGy.

The third equivalent dose level and the fourth equivalent dose level may vary according to clinical demands. For example, in a liver scan, a ratio of the fourth equivalent dose level to the third equivalent dose level may range from 5% to 40%, such as 10%, 15%, 20%, 25%, 30%, 50%, 85%, etc. In an epigastrium scan, a ratio of the fourth equivalent dose level to the third equivalent dose level may range from equal to or exceed 10%, or 15%, or 25%, or 30%, or 40%, or 50%, 85%, etc. For example, for a CBCT scan, the ratio of the fourth equivalent dose level to the third equivalent dose level may equals to or exceeds 1:3, or 1:2. For a CT scan, the ratio of the fourth equivalent dose level to the third equivalent dose level may equal to 1:7, or 1:5.

In 708, the general neural network model for denoising may be trained using the training data of the second subject to obtain a personalized neural network model for denoising. Operation 708 may be performed by the neural network model determination unit 502.

In some embodiments, multiple pairs of image blocks may be extracted from the high-dose image and the low-dose image relating to the second subject as the training data of the general neural network model for denoising. As used herein, each pair of the multiple pairs of image blocks may include a first image block extracted from the high-dose image and a second image block extracted from the low-dose image. The first image block and the second image block may correspond to the same region in the ROI of the second subject. In some embodiments, the first image block and/or the second image block may be extracted based on a random sampling algorithm. Exemplary random sampling algorithms may include an acceptance-rejection sampling algorithm, an importance sampling algorithm, a Metropolis-Hasting algorithm, a Gibbs sampling algorithm, etc. In some embodiments, the first image block and/or the second image block may be extracted based on an instruction provided by a user via the terminal(s) 140.

The general network model for denoising may be trained based on the multiple pairs of image blocks using a machine training algorithm as described above. In some embodiments, a cost function (e.g., a lost function) may be used to training the general neural network model for denoising. The cost function may be configured to assess a difference between a testing value (e.g., the second image block of the low-dose image) and a desired value (e.g., the first image block of the high-dose image). In some embodiments, the second image block of the low-dose image may be inputted to the general neural network model for denoising via an input layer (e.g., the input layer 1120 as illustrated in FIG.

Figure 12:
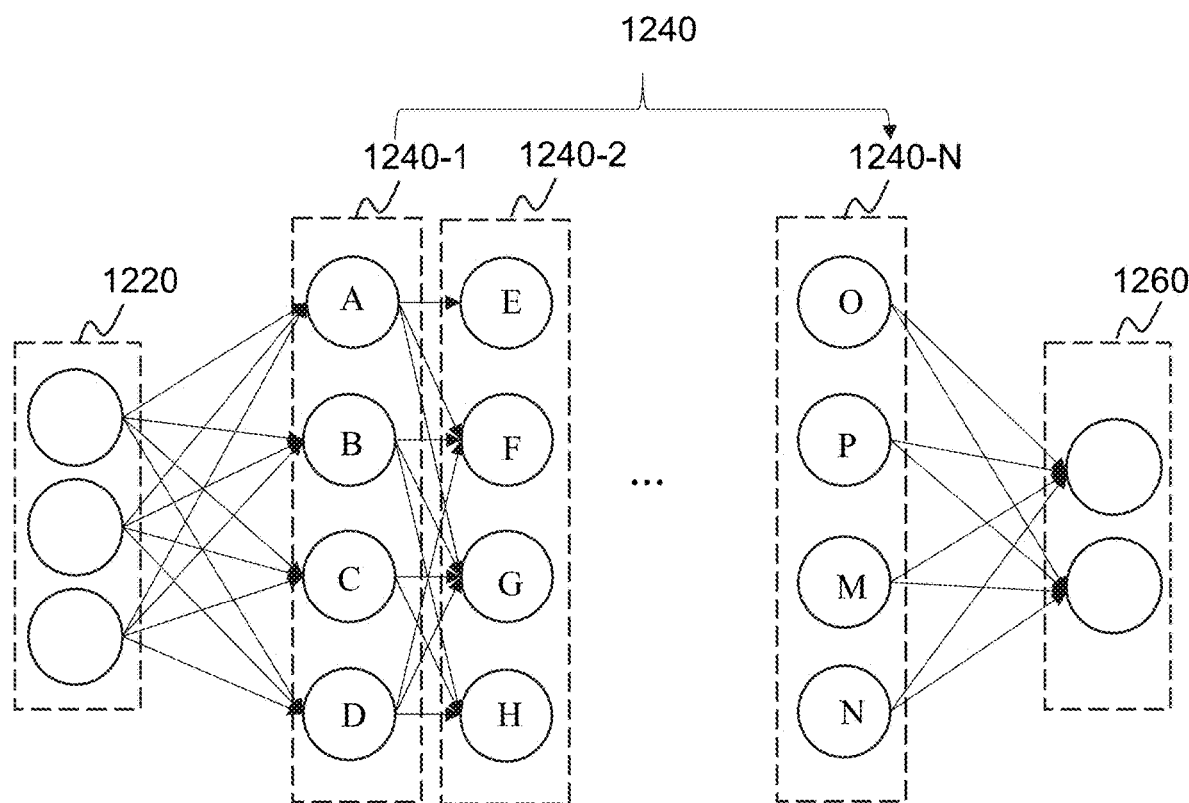
FIG. 12 is a schematic diagram illustrating an exemplary convolutional neural network (CNN) model according to some embodiments of the present disclosure.

12). The second image block of the low-dose image may be transferred from a first hidden layer of the neural network model (e.g., the conventional layers 1140-1 as illustrated in FIG. 12) to the last hidden layer of the general neural network model for denoising. The second image block of the low-dose image may be processed in each of the multiple hidden layers via performing an image transformation operation, an image enhancement operation, an image denoising operation, or any other operations. The processed second image block of the low-dose image processed by the hidden layers may be inputted to the cost function layer. The value of the cost function may be determined based on the processed the second image block of the low-dose image and the first image block of the high-dose image. Then, a parameter (e.g., a weigh value) of the general neural network model for denoising may be adjusted in the training process until the value of the cost function satisfies a condition (e.g., a predetermined threshold).

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, operations 702 and 706 may be performed simultaneously or in a reverse order than that illustrated in FIG. 7, and/or operations 704 and 706 may be performed simultaneously or in a reverse order than that illustrated in FIG. 7. As another example, operations 702 and 704 may be omitted. The personalized neural network model for denoising may be determined by training a neural network model based on the training data relating to the second subject. In some embodiments, process 700 may further include storing the training data of the second subject and/or the multiple groups of training data relating to multiple first subjects in the storage 130, the terminals 140, the storage module 450, the storage unit 580, and/or other external storage devices.

FIG. 8 is a flowchart illustrating an exemplary process 800 for processing low-dose image based on a neural network model for denoising according to some embodiments of the present disclosure. In some embodiments, one or more operations of process 800 illustrated in FIG. 8 may be implemented in the diagnostic and treatment system 100 illustrated in FIG. 1. For example, the process 800 illustrated in FIG. 8 may be stored in the storage 130 in the form of instructions, and invoked and/or executed by the processing device 120 (e.g., the processor 210 of the computing device 200 as illustrated in FIG. 2, the GPU 330 or CPU 340 of the mobile device 300 as illustrated in FIG. 3). Operation 608 may be performed according to process 800.

In 802, a low-dose image relating to an ROI of a subject may be processed using the neural network model for denoising to determine noise data included in the low-dose image data. Operation 802 may be performed by the imaging data denoising unit 504. The low-dose image (e.g., the first image data obtained in 602) relating to the ROI of the subject may correspond to a low-dose level (e.g., the first equivalent dose level as descried in 602). The low-dose image may exhibit a quality of image lower than that of high-dose image (e.g., the second image data as described in 608) corresponding to the low-dose image. As used herein, the quality of image may be defined by a noise level of the image. The noise level of the low-dose image may be higher than that of high-dose image corresponding to the low-dose image data. The neural network model for denoising may be used to extract the noise data from the low-dose image. The noise data extracted from the low-dose image using the neural network model for denoising may include a noise image representing noises included in the low-dose image.

The neural network model for denoising may be obtained from the storage 130, the storage module 408, the storage unit 508, or other external storage. In some embodiments, the neural network model for denoising may be pre-determined (e.g., provided by a manufacturer of an IGRT apparatus, an entity specializing in image processing, an entity having access to training data, etc.). In some embodiments, the neural network model for denoising may be determined according to process 700 as illustrated in FIG. 7. In some embodiments, the neural network model for denoising may include a general neural network model for denoising or a personalized neural network model for denoising corresponding to the subject.

In 804, a high-dose image relating to the ROI of the subject may be determined based in the noise data and the low-dose image. Operation 804 may be performed by the imaging data denoising unit 504. The high-dose image (e.g., the second image data obtained in 608) may be determined by a combination of noise data and the low-dose image (e.g., the first image data obtained in 602). Further, the high-dose image (e.g., the second image data obtained in 608) may be determined by performing a subtraction operation between the noise data (e.g., the noise image) and the low-dose image. For example, the noise data (e.g., the noise image) may include a plurality of first pixels or voxels. The low-dose image (e.g., the first image data obtained in 602) may include a plurality of second pixels or voxels. The high-dose image (e.g., the second image data obtained in 608) may include a plurality of third pixels or voxels. A gray value of a third pixel or voxel in the high-dose image may be equal to a subtraction between a gray value of a corresponding pixel or voxel in the low-dose image and a gray value of a corresponding pixel or voxel in the noise image. As used herein, the corresponding pixel or voxel in the low-dose image, the high-dose image, and the noise image may refer to three pixels or voxels that represent the same spatial point or region of the ROI of the subject.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, operation 802 may be omitted. The low-dose image may be converted to the high-dose image directly using the neural network model for denoising. In some embodiments, the neural network model for denoising may be configured to extract the noise data from low-dose projection data. The noise data may be converted to a noise image. The low-dose projection data may be processed to obtain a low-dose image. The high-dose image may be determined based on the reconstructed low-dose image and the noise image.

Figure 9:
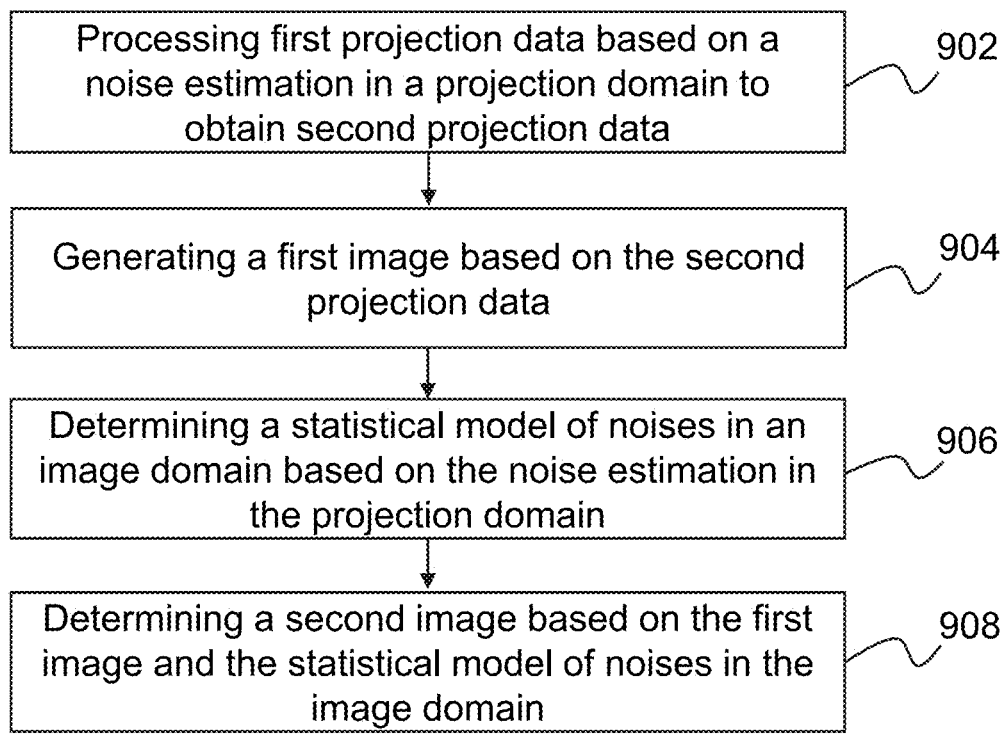
FIG. 9 is a flowchart illustrating an exemplary process for processing low-dose image data based on a statistical model of noises according to some embodiments of the present disclosure.

FIG. 9 is a flowchart illustrating an exemplary process 900 for processing low-dose image data based on a statistical model of noises according to some embodiments of the present disclosure. In some embodiments, one or more operations of process 900 illustrated in FIG. 9 may be implemented in the diagnostic and treatment system 100 illustrated in FIG. 1. For example, the process 900 illustrated in FIG. 9 may be stored in the storage 130 in the form of instructions, and invoked and/or executed by the processing device 120 (e.g., the processor 210 of the computing device 200 as illustrated in FIG. 2, the GPU 330 or CPU 340 of the mobile device 300 as illustrated in FIG. 3). Operation 608 may be performed according to process 900.

In 902, first projection data may be processed based on a noise estimation in a projection domain to obtain second projection data. Operation 902 may be performed by the iterative reconstruction unit 506. The first projection data may include low-dose projection data corresponding to a first equivalent dose level (e.g., the first equivalent dose level of the first image data obtained in 602). The low-dose projection data (the first image data obtained in 602) may be obtained from the IGRT apparatus 110, the storage module 408, the storage unit 508, or other storages as described in connection with operation 602. The noise estimation may be obtained from the storage 130, the storage module 408, the storage unit 508, or other storages as described in connection with 604. The noise estimation may represent a noise level of the first projection data. The noise estimation may be determined based on the first projection data and/or according a default setting of the diagnostic and treatment system 100 as described elsewhere in the disclosure. See, for example, FIG. 6 and the description thereof.

In some embodiments, the first projection data may be denoised based on the noise estimation using a nonlinear filtering algorithm. Exemplary nonlinear filtering algorithms may include an extended Calman filter (EKF) algorithm, an unscented filter Calman (UFK) algorithm, a particle filter (PF) algorithm, etc. For example, the nonlinear filtering algorithm may be performed based on an objective function represented by Equation (1) as below:

$$\text{minimize}\{\int|\nabla n|+\beta^*(\delta_n(\gamma,\xi))^{-b}*\int(n(\gamma,\xi)-n_0(\gamma,\xi))^2 dx\}, \quad (1),$$

where, $n(\gamma,\xi)$ denotes the second projection data, $n_0(\gamma,\xi)$ denotes the first projection data, $\nabla n$ denotes a total variation, $(\delta_n(\gamma,\xi))^{-b}$ denotes the noise estimation relating to the first projection data, $\beta$ denotes a parameter configured to adjust a strength of denoising, $\gamma$ denotes a channel count of a detector in an imaging device (e.g., the imaging device 112 of the IGRT apparatus 110), $\xi$ denotes a row count of the detector in the imaging device (e.g., the imaging device 112 of the IGRT apparatus 110), and b denotes a constant. For instance, b may be a constant in the range from 0 to 5, such as 0, 0.5, 1, 1.5, 2, 2.5, 3, 3.5, 4, 4.5, or 5. As illustrated in Equation (1), the second projection data may be determined by performing a plurality of iterations based on the objective function (i.e., Equation (1)) until a condition is satisfied. An exemplary condition is that the value of the objective function (i.e., Equation (1)) is at least locally minimum when the condition is satisfied. Merely by way of example, the condition is that the value of the objective function (i.e., Equation (1)) is globally minimum when the condition is satisfied. Another exemplary condition is that a specified number of iterations are performed. A further exemplary condition is that the change of the value of the objective function in two or more consecutive iterations may be equal to or smaller than a threshold. The strength of denoising for the first projection data may be controlled by the noise estimation and the value of $\beta$. The greater the product between $(\delta_n(\gamma,\xi))^{-b}$ and $\beta$ is, the smaller the strength of denoising for the first projection data may be. The greater the noise level of the first projection data is, the smaller the value of $(\delta_n(\gamma,\xi))^{-b}$ may be, the smaller the product between $(\delta_n(\gamma,\xi))^{-b}$ and $\beta$ may be, and the greater the strength of denoising for the first projection data may be.

In 904, a first image may be generated based on the second projection data. Operation 904 may be performed based on the iterative reconstruction unit 506. In some embodiments, the first image may be generated based on the second projection data using an image reconstruction algorithm. Exemplary image reconstruction algorithms may include a filtered back projection (FBP) algorithm, an algebraic reconstruction technique (ART), a local reconstruction algorithm, or the like, or a combination thereof.

In 906, a statistical model of noises in an image domain may be determined based on the noise estimation in the projection domain. Operation 906 may be performed based on the iterative reconstruction unit 506. In some embodiments, the statistical model of noises in the image domain may be determined by performing a back projection operation on the noise estimation in the projection domain. Further, the noise estimation in the projection domain may be also referred to as noise projection data. The statistical model of noises in the image domain may be also referred to as a noise image. The noise image may be generated based on the noise projection data using a filtered back projection (FBP) algorithm. More descriptions of the statistical model of noises in the image domain and/or the noise estimation in the projection domain may be found in, for example, Chinese Publication No 1039713876, entitled "SYSTEM AND METHOD FOR CT IMAGE RECONSTRUCTION," the contents of which are hereby incorporated by reference.

In 908, a second image may be determined based on the first image and the statistical model of noises in the image domain. Operation 908 may be performed based on the iterative reconstruction unit 506. In some embodiments, the first image may be denoised based on the statistical model of noises in the image domain using a nonlinear filtering algorithm as described above. Further, the nonlinear filtering algorithm may be performed based on an objective function represented by Equation (2) as below:

$$\text{minimize}\{\int|\nabla u|dxdy+\beta^*(\delta_u(x,y))^{-b}*\int(u(x,y)-u_0(x,y))^2 dxdy\} \quad (2),$$

where $u_0(x,y)$ denotes a gray value of a pixel value in the first image, $u(x,y)$ denotes a gray value of a pixel in the second image, $\nabla u$ denotes a total variation of the second image, $(\delta_u(x,y))^{-b}$ denotes the statistical model of noises in the image domain, $\beta$ denotes a parameter relating the statistical model of noises in the image domain configured to adjust a strength of denoising, b denotes a constant, such as −2, −2.5, or −3. As illustrated in Equation (2), the second image may be determined by performing a plurality of iterations based on the objective function (i.e., Equation (2)) until a condition is satisfied. An exemplary condition is that the value of the objective function (i.e., Equation (2)) is at least locally minimum when the condition is satisfied. Merely by way of example, the condition is that the value of the objective function (i.e., Equation (1)) is globally minimum when the condition is satisfied. Another exemplary condition is that a specified number of iterations are performed. A further exemplary condition is that the change of the value of the objective function in two or more consecutive iterations may be equal to or smaller than a threshold. The strength of denoising for the first image may be controlled by the statistical model of noises in the image domain and the value of $\beta$. The greater the product between $(\delta_u(x,y))^{-b}$ and is, the smaller the strength of denoising for the first image may be. The greater the noise level of the first image is, the smaller the value of $(\delta_u(x,y))^{-b}$ may be, the smaller the product between $(\delta_u(x,y))^{-b}$ and $\beta$ may be, and the greater the strength of denoising for the first image may be.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, the low-dose image data and the high-dose image data may include low-dose projection data and the high-dose projection data, respectively. For example, process 900 may include pre-processing the first projection data. As another example, operations 904 and 906 may be performed simultaneously or in a reverse order than that illustrated in FIG. 9.

Figure 10:
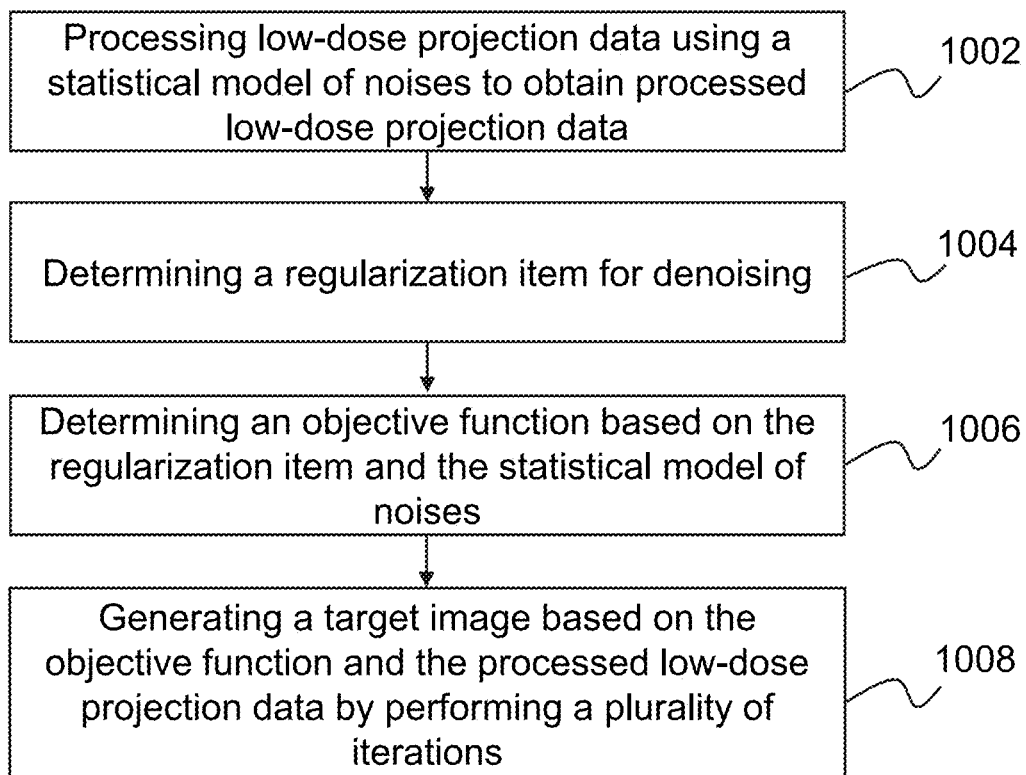
FIG. 10 is a flowchart illustrating an exemplary process for processing low-dose image data based on an iterative reconstruction technique according to some embodiments of the present disclosure.

FIG. 10 is a flowchart illustrating an exemplary process 1000 for processing low-dose image data based on an iterative reconstruction technique according to some embodiments of the present disclosure. In some embodiments, one or more operations of process 1000 illustrated in FIG. 10 may be implemented in the diagnostic and treatment system 100 illustrated in FIG. 1. For example, the process 900 illustrated in FIG. 10 may be stored in the storage 130 in the form of instructions, and invoked and/or executed by the processing device 120 (e.g., the processor 210 of the computing device 200 as illustrated in FIG. 2, the GPU 330 or CPU 340 of the mobile device 300 as illustrated in FIG. 3). Operation 608 may be performed according to process 1000.

In 1002, low-dose projection data may be processed using a statistical model of noises. Operation 1002 may be performed by the iterative reconstruction unit 504. The statistical model of noises may be obtained as described in connection with operation 604.

In 1004, a regularization item for denoising may be determined. Operation 1004 may be performed by the iterative reconstruction unit 506. As used herein, the regularization item (e.g., βR(X) in Equation (3)) may refer to an item that may be used to regularize image estimate(s) generated during an iterative reconstruction process. In some embodiments, the regularization item may be defined by a regularization parameter and a regularization function. For example, the regularization item may be determined by multiplying the regularization parameter and the regularization function. In some embodiments, the regularization item may relate to a denoising model (e.g., the statistical model of noises). For example, the regularization parameter may control the strength of the regularization item (also referred to as the intensity for denoising) based on the denoising model (e.g., the statistical model of noises). In some embodiments, the regularization item may be determined based on a sparsity of low-dose projection data. In some embodiments, the low-dose projection data may be represented by a matrix including a plurality of elements. The sparsity of the low-dose projection data may refer to a ratio of the number of zero-valued elements to the total number of the plurality of elements in the matrix of the low-dose projection data. Further, the regularization parameter may be determined based on the sparsity of low-dose projection data. The greater the sparsity of low-dose projection data is, the greater the regularization parameter may be.

The regularization parameter may be used to control the strength of the regularization item (also referred to as the intensity for denoising). In some embodiments, the regularization parameter may include a set of elements. The regularization parameter may be expressed in the form of a matrix. Each of the set of elements may correspond to an element in an image estimate. For example, if an image estimate has 8×9 pixels, the regularization parameter may include 72 elements. Each of the 72 elements may correspond to a pixel of the image estimate. In some embodiments, the regularization parameter may be determined based on the statistical model of noises in the image domain. For example, the greater the element in the statistical model of noises is, the greater the corresponding element in the regularization parameter may be. As used herein, an element in the statistical model of noises and a corresponding element in the regularization parameter may refer to two elements corresponding to a same pixel in an image estimate.

In 1006, an objective function may be determined based on the regularization item and the statistical model of noises. Operation 1006 may be performed by the iterative reconstruction unit 506. In some embodiments, the objective function may be determined based on a least squares technique. The least squares technique may be used to determine an optimal solution that at least locally minimizes the sum of the squares of the difference between a value estimate and an observed value. As used herein, an optimal solution may refer to a target image, the value estimate may refer to a projection estimate corresponding to an image estimate generated in an iteration, and the observed value may refer to the low-dose projection data. As used herein, the sum of the squares of the difference between a value estimate and an observed value may be considered locally minimum when, for example, a value of the objective function is smaller than a constant, a specified number of iterations are performed, the objective function converges, etc.

For illustration purposes, the objective function may be expressed by the following Equation (3):

$$f(X) = \min_{X \geq 0} \|AX - Y\|_w^2 + \beta R(X), \qquad (3)$$

where f(X) denotes the objective function, X denotes an image to be reconstructed (also referred to as an image estimate, or a target image), Y denotes the processed low-dose projection data, A denotes a projection matrix, βR(X) denotes a regularization item, β denotes a regularization parameter (also referred to as a penalty coefficient), R(X) denotes a regularization function, w denotes a statistical weight (e.g., a constant) determined based on the statistical model of noises as described elsewhere in the disclosure, and $$\min_{X \geq 0}$$

denotes a preset condition or a constraint.

In 1008, a target image may be generated based on the objective function and the low-dose projection data by performing a plurality of iterations. Operation 1008 may be performed by the iterative reconstruction unit 506. The objective function may be used to determine the target image (also referred to as an optimal image) by globally minimizing a value of the objective function. In some embodiments, the plurality of iterations may be performed according to process 1100 as described in connection with FIG. 11. In some embodiments, an image estimate may be determined in an iteration. A projection estimate corresponding to the image estimate may be determined by projecting the image estimate onto a specific projection plane. The projection estimate may be compared with the processed low-dose projection data, and a target image may be determined by updating the image estimate based on a difference between the projection estimate and the processed low-dose projection data.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, process 1000 may include pre-processing the low-dose projection data. As another example, operations 1004 and 1006 may be performed simultaneously or in a reverse order than that illustrated in FIG. 10.

Figure 11:
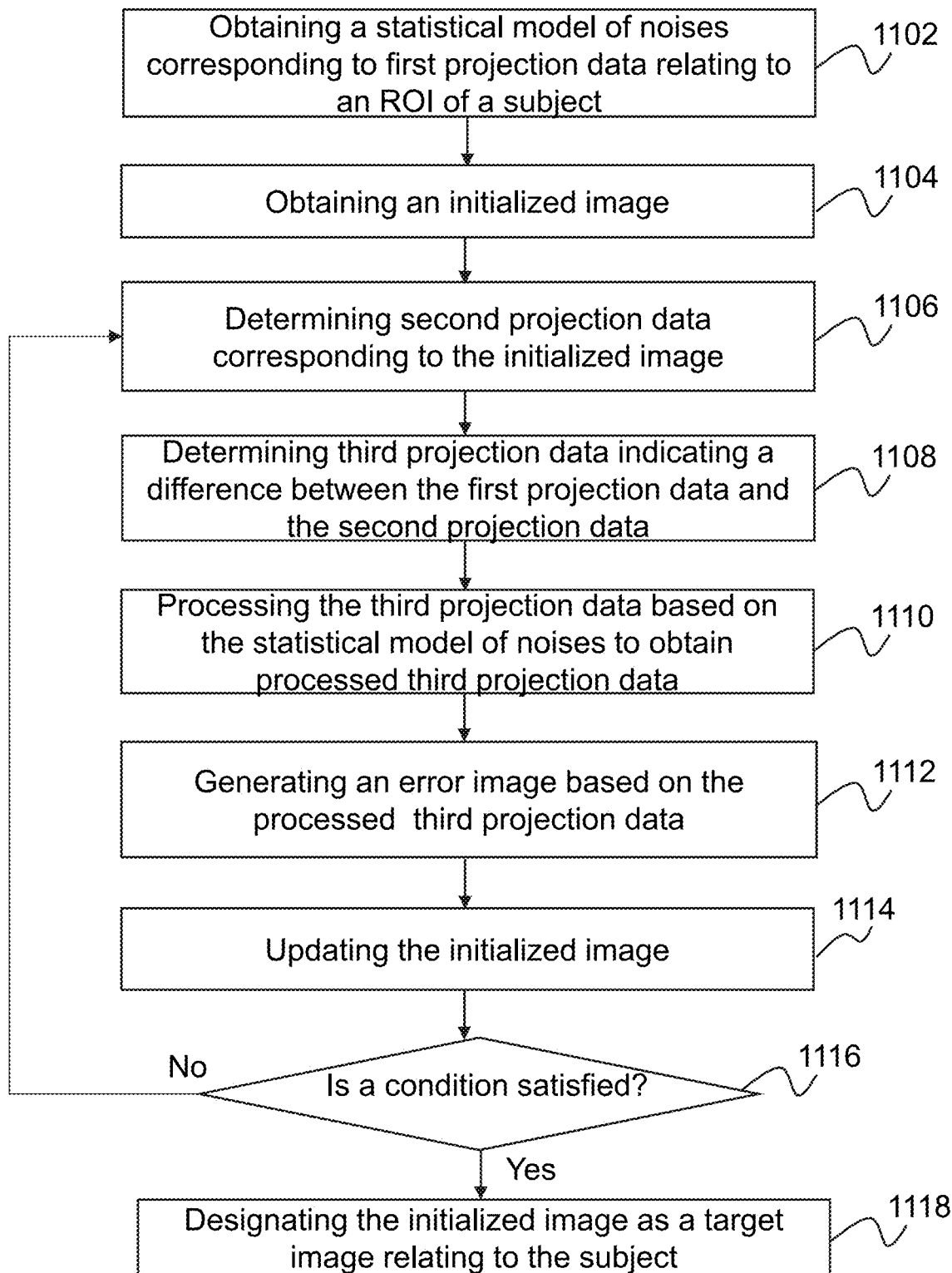
FIG. 11 is a flowchart illustrating an exemplary process for processing low-dose image data based on an iterative reconstruction technique according to some embodiments of the present disclosure.

FIG. 11 is a flowchart illustrating an exemplary process 1100 for processing low-dose image data based on an iterative reconstruction technique according to some embodiments of the present disclosure. In some embodiments, one or more operations of process 1100 illustrated in FIG. 11 may be implemented in the diagnostic and treatment system 100 illustrated in FIG. 1. For example, the process 1100 illustrated in FIG. 11 may be stored in the storage 130 in the form of instructions, and invoked and/or executed by the processing device 120 (e.g., the processor 210 of the computing device 200 as illustrated in FIG. 2, the GPU 330 or CPU 340 of the mobile device 300 as illustrated in FIG. 3). Operation 1008 may be performed according to process 1100.

In 1102, a statistical model of noises corresponding to first projection data relating to an ROI of a subject may be obtained. Operation 1102 may be performed by the acquisition module 402. The statistical model of noises may be obtained from the storage 130, the storage module 408, the storage unit 508, the terminal(s) 140, or other storages. The statistical model of noises may be determined as described elsewhere in the present disclosure. See, for example, FIGS. 6, 9, and 10 and the descriptions thereof. The first projection data may include the processed low-dose projection data determined as described in connection with FIG. 10.

In 1104, an initialized image may be obtained. Operation 1104 may be performed by the iterative reconstruction unit 506. In some embodiments, the initialized image may include a plurality of pixels or voxels with estimated characteristics, such as gray value, intensity, color, etc. In some embodiments, the initialized image may be predetermined by a user via the terminal(s) 140 or according to a default setting of the diagnostic and treatment system 100. In some embodiments, the gray values of pixels or voxels in the initialized image may be set as different values or the same value. For example, the gray values of pixels or voxels in the initial image estimate may be set as 0. In some embodiments, the initialized image may be determined by performing a filtered back projection (FBP) operation on the first projection data.

In 1106, second projection data corresponding to the initialized image may be determined. Operation 1106 may be performed by the iterative reconstruction unit 506. The second projection data corresponding to the initialized image may be determined by projecting the initialized image onto a specific projection plane. In some embodiments, the second projection data may be determined based on the initialized image and a projection matrix. For example, the second projection data may be determined by multiplying the projection matrix by the initialized image. In some embodiments, the projection matrix may be predetermined according to a default setting of the diagnostic and treatment system 100, or may be adjusted by a user (e.g., a doctor).

In 1108, third projection data indicating a difference between the first projection data and the second projection data may be determined. Operation 1108 may be performed by the iterative reconstruction unit 506. In some embodiments, the third projection data may be determined based on a subtraction of the first projection data and the second projection data.

In 1110, the third projection data may be processed based on the statistical model of noises to obtain processed third projection data. Operation 1010 may be performed by the iterative reconstruction unit 506. In some embodiments, the third projection data may include a plurality of subsets of data. The plurality of subsets of data may be represented by a first matrix. The statistical model of noises may be represented by a second matrix. The second matrix may include a weighting matrix including a plurality of weighting factors in a range from 0 to 1. The processed third projection data may be determined by performing a dot product of the first matrix and the second matrix. As used herein, the dot product of the first matrix and the second matrix may be determined by multiplying a total amount of data in each of the plurality of the subsets of data and the corresponding weighting factor in the second matrix. For example, if the weighting factor is 1, the whole subset of data may be included in the processed third projection data. As another example, if the weighting factor is 0.5, the subset of data multiplied by 0.5 may be included in the processed third projection data. As still another example, if the weighting factor is 0, the whole subset of data may be excluded from the processed third projection data.

In 1112, an error image is determined based on the processed third projection data. Operation 1112 may be performed by the iterative reconstruction unit 506. The error image may be generated by performing a back projection operation on the processed third projection data.

In 1114, the initialized image may be updated. Operation 1114 may be performed by the iterative reconstruction unit 506. In some embodiments, a plurality of iterations may be performed based on the objective function. While in an iteration other than the first iteration, the initialized image may be updated based on a reconstructed image (e.g., an image estimate) generated in a previous iteration based on the first projection data.

In 1116, a determination may be made as to whether a condition is satisfied. Operation 1116 may be performed by the iterative reconstruction unit 506. If the condition is satisfied, process 1100 may proceed to operation 1118. If the condition is not satisfied, process 1100 may proceed to operation 1106. In some embodiments, the condition may be assessed based on a value of the objective function or the error image generated in an iteration. For example, the condition may include that the value of the objective function may be minimal or smaller than a threshold, the change of the value of the objective function in two or more consecutive iterations may be equal to or smaller than a threshold, the difference between the value of the objective function and a target value is equal to or smaller than a threshold, etc. As another example, the condition may include that the change of the average gray value of pixels or voxels in the error image generated in two or more consecutive iterations may be equal to or smaller than a threshold, such as 0, or the difference between the average gray value of pixels or voxels in the error image and a target value is below a threshold. In some embodiments, the condition may be satisfied when a specified number of iterations are performed.

In 1118, the initialized image may be designated as a target image relating to the subject. Operation 1118 may be performed by the iterative reconstruction unit 506. The target image may correspond to an optimal solution of the objective function. The target image may correspond to a dose level higher than that of the first projection data.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, process 1100 may include pre-processing the first projection data. As another example, operations 1104 and 1106 may be performed simultaneously or in a reverse order than that illustrated in FIG. 11. It may be indicated that the iteration process 1100 may terminate after the condition is satisfied.

FIG. 12 is a schematic diagram illustrating an exemplary convolutional neural network (CNN) model according to some embodiments of the present disclosure.

The CNN model may include an input layer 1220, multiple hidden layers 1240, and an output layer 1260. The multiple hidden layers 1240 may include one or more convolutional layers, one or more Rectified Linear Units layers (ReLU layers), one or more pooling layers, one or more fully connected layers, or the like, or a combination thereof.

For illustration purposes, exemplary hidden layers 1240 of the CNN model, including a convolutional layer 1240-1, a pooling layer 1240-2, and a fully connected layer 1240-N, are illustrated. As described in connection with process 700, the model determination unit 502 may acquire low-dose image as an input of the CNN model. The low-dose image may be expressed as a two-dimensional (2D) or three-dimensional (3D) matrix including a plurality of elements (e.g., pixels or voxels). Each of the plurality of elements in the matrix may have a value (also referred to as pixel/voxel value) representing a characteristic of the element.

The convolutional layer 1240-1 may include a plurality of kernels (e.g., A, B, C, and D). The plurality of kernels may be used to extract features of the low-dose image data. In some embodiments, each of the plurality of kernels may filter a portion (e.g., a region) of the low-dose image to produce a specific feature corresponding to the portion of the low-dose image data. The feature may include a low-level feature (e.g., an edge feature, a texture feature), a high-level feature, or a complicated feature that is calculated based on the kernel(s).

The pooling layer 1240-2 may take the output of the convolutional layer 1240-1 as an input. The pooling layer 1240-2 may include a plurality of pooling nodes (e.g., E, F, G, and H). The plurality of pooling nodes may be used to sample the output of the convolutional layer 1240-1, and thus may reduce the computational load of data processing and increase the speed of data processing of the diagnostic and treatment system 100. In some embodiments, neural network model determination unit 502 may reduce the volume of the matrix corresponding to the low-dose image in the pooling layer 1240-2.

The fully connected layer 1240-N may include a plurality of neurons (e.g., 0, P, M, and N). The plurality of neurons may be connected to a plurality of nodes from the previous layer, such as a pooling layer. In the fully connected layer 1240-N, a plurality of vectors corresponding to the plurality of neurons may be determined based on the features of the low-dose image and further weigh the plurality of vectors with a plurality of weighting coefficients.

In the output layer 1260, an output, such a noise data (e.g., a noise image) may be determined based on the plurality of vectors and weighting coefficients obtained in the fully connected layer 1240-N.

It shall be noted that the CNN model may be modified when applied in different conditions. For example, in a training process, a loss function (also referred to as a cost function) layer may be added to specify the deviation between a predicted output (e.g., a predicted noise image) and a true label (e.g., reference high-dose image corresponding to the low-dose image).

In some embodiments, the neural network model determination unit 502 may get access to multiple processing units, such as GPUs, in the diagnostic and treatment system 100. The multiple processing units may perform parallel processing in some layers of the CNN model. The parallel processing may be performed in such a manner that the calculations of different nodes in a layer of the CNN model may be assigned to two or more processing units. For example, one GPU may run the calculations corresponding to kernels A and B, and the other GPU(s) may run the calculations corresponding to kernels C and D in the convolutional layer 1240-1. Similarly, the calculations corresponding to different nodes in other type of layers in the CNN model may be performed in parallel by the multiple GPUs.

EXAMPLES

The examples are provided for illustration purposes, and not intended to limit the scope of the present disclosure.

Example 1. Exemplary Images Corresponding to Different Dose Levels

Figures 13A, 13B:
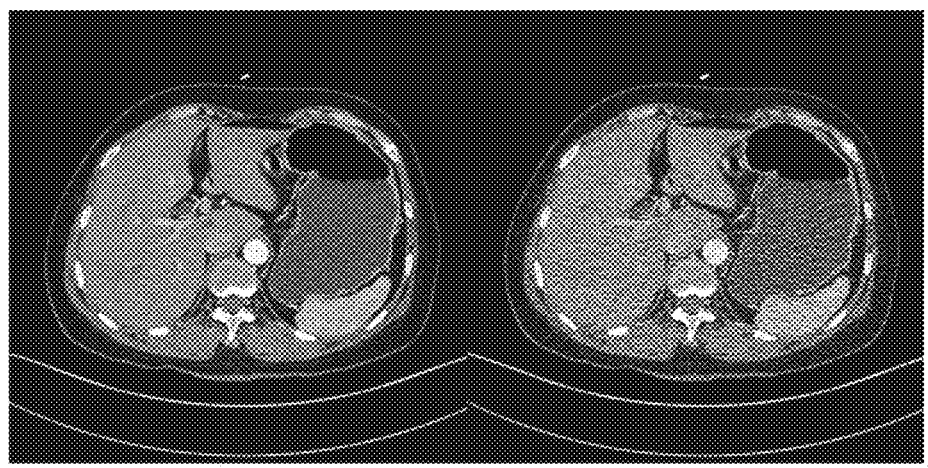
FIG. 13A and FIG. 13B illustrate exemplary images corresponding to different dose levels according to some embodiments of the present disclosure.

FIG. 13A and FIG. 13B illustrate exemplary images corresponding to different dose levels according to some embodiments of the present disclosure. The first image shown in FIG. 13A and the second image shown in FIG. 13B represent the same abdomen of a subject. The first image corresponds to a first equivalent dose level. The second image corresponds to a second equivalent dose level lower than 85% of the first equivalent dose level. The noise level shown in the second image is greater than that shown in the first image.

Example 2. Exemplary Images Corresponding to Different Dose Levels

Figures 14A, 14B, 14C:
FIGS. 14A-14C illustrate exemplary images corresponding to different dose levels according to some embodiments of the present disclosure.

FIG. 14A and FIG. 14B illustrate exemplary images corresponding to different dose levels according to some embodiments of the present disclosure. The first image shown in FIG. 14A, the second image shown in FIG. 14B, and the third image shown in FIG. 14C represent the same ROI of a subject. The first image corresponds to a first equivalent dose level. The second image corresponds to a second equivalent dose level higher than the first equivalent dose level. The second image was generated based on the first image using a neural network model for denoising according to process 800. The third image corresponds to a third equivalent dose level higher than 85% of the first equivalent dose level. The noise level shown in the second image is lower than those shown in the first image and the third image.

Figures 15A, 15B, 15C:
FIGS. 15A-15C illustrate exemplary images corresponding to different dose levels generated based on different reconstruction algorithms according to some embodiments of the present disclosure.

Example 3. Exemplary Images Corresponding to Different Dose Levels Generated Based on Different Reconstruction Algorithms FIGS. 15A-15C illustrate exemplary images corresponding to different dose levels generated based on different reconstruction algorithms according to some embodiments of the present disclosure. The first image shown in FIG. 15A, the second image shown in FIG. 15B, and the third image shown in FIG. 15C represent the same ROI of a subject. The first image corresponds to a first equivalent dose level. The first image was generated based on a FBP reconstruction algorithm. The second image corresponds to a second equivalent dose level. The second equivalent dose level was 55% of the first equivalent dose level. The second image was generated based on the FBP reconstruction algorithm. The third image corresponds to a third equivalent dose level same as the second equivalent dose level. The third image was generated based on a Karl reconstruction algorithm according to process 900 as illustrated in FIG. 9. The noise level shown in the third image is lower than those shown in the first image and the second image.

Figures 16A, 16B:
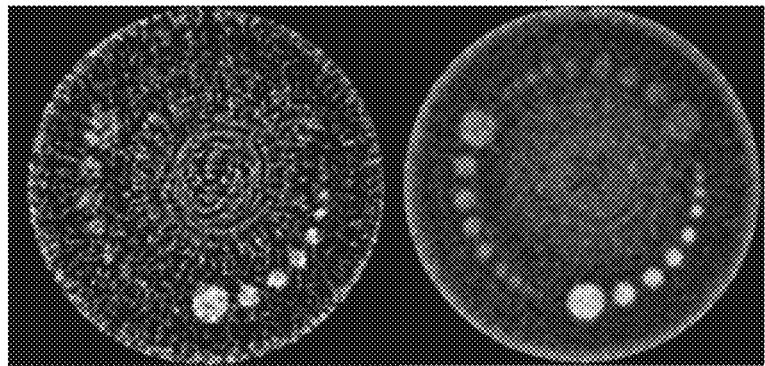
FIGS. 16A and 16B illustrate exemplary images corresponding to the same dose level generated based on different reconstruction algorithms according to some embodiments of the present disclosure.

Example 4. Exemplary Images Corresponding to the Same Dose Level Generated Based on Different Reconstruction Algorithms FIGS. 16A and 16B illustrate exemplary images corresponding to the same dose level generated based on different reconstruction algorithms according to some embodiments of the present disclosure. The first image shown in FIG. 16A and the second image shown in FIG. 16B represent the same ROI of a subject. The first image corresponds to a first equivalent dose level. The first image was generated based on a FBP reconstruction algorithm. The second image corresponds to a second equivalent dose level same as the first equivalent dose level. The second image was generated based on the iterative reconstruction algorithm according to process 1000 and/or 1100. The noise level shown in the second image is lower than that shown in the first image.

Figures 17A, 17B, 17C:
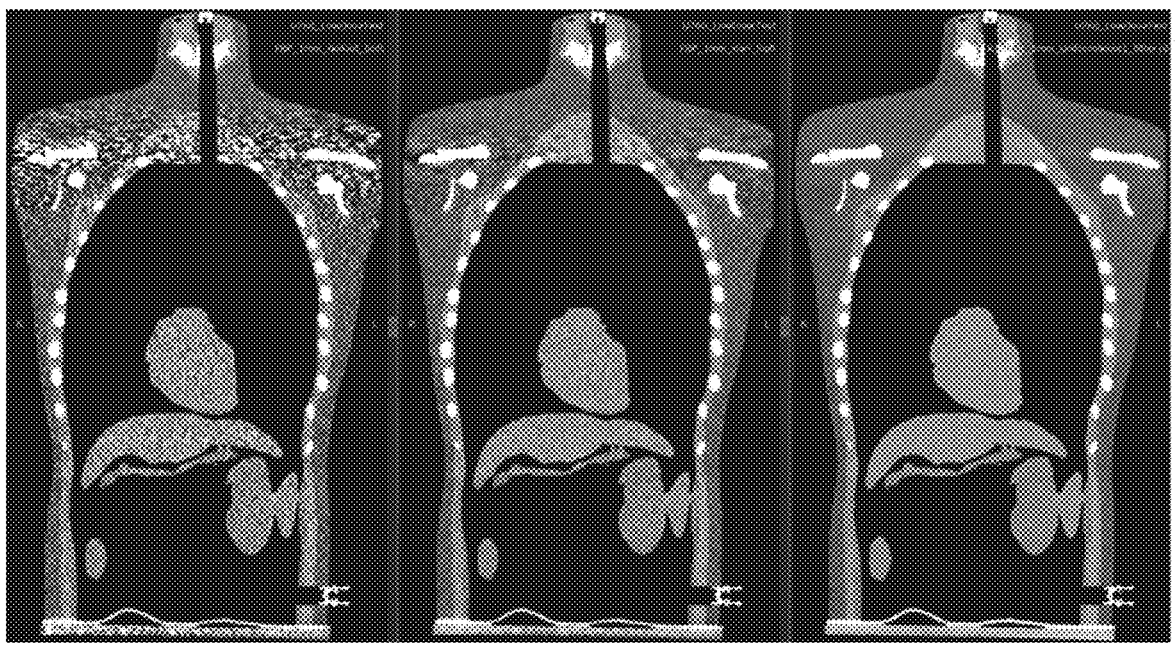
FIGS. 17A-17C illustrate exemplary images corresponding to the same dose level generated based on different reconstruction algorithms according to some embodiments of the present disclosure.

Example 5. Exemplary Images Corresponding to the Same Dose Level Generated Based on Different Reconstruction Algorithms FIGS. 17A-17C illustrate exemplary images corresponding to the same dose level generated based on different reconstruction algorithms according to some embodiments of the present disclosure. The first image shown in FIG. 17A, the second image shown in FIG. 17B, and the third image shown in FIG. 17C represent a body phantom of a head. The dose level of the first image, the second image, and the third image is same. The first image was generated based on a FBP reconstruction algorithm. The second image was generated based on according to process 900 as illustrated in FIG. 9. The third image was generated based on an iterative reconstruction algorithm according to process 1000 and/or 1100. The noise level shown in the third image is lower than that shown in the first image and the second image.

Example 6. Exemplary Images Corresponding to the Same Dose Level Generated Based on Different Reconstruction Algorithms FIGS. 18A and 18B illustrate exemplary images corresponding to the same dose level generated based on different reconstruction algorithms according to some embodiments of the present disclosure. The first image shown in FIG. 18A and the second image shown in FIG. 18B represents the same ROI of a subject. The dose level of the first image and the second image are same. The first image was generated according to process 900 as illustrated in FIG. 9. The second image was generated according to process 1000 and/or 1100 as illustrated in FIG. 10 and/or FIG. 11. The noise level shown in the second image is lower than that shown in the first image.

Example 7. Exemplary Images Corresponding to the Same Dose Level Generated Based on Different Reconstruction Algorithms FIGS. 19A and 19B illustrate exemplary images corresponding to the same dose level generated based on different reconstruction algorithms according to some embodiments of the present disclosure. The first image shown in FIG. 19A and the second image shown in FIG. 19B represented the same ROI of a body. The dose level of the first image and the second image are same. The first image was generated according to process 1000 as illustrated in FIG. 10. The second image was generated according to process 1000 and/or 1100 as illustrated in FIG. 10 and/or FIG. 11. The second image was generated further based on sparsity of projection data corresponding to the second image. The noise level shown in the second image is lower than that shown in the first image.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in a combination of one or more programming languages, including an object oriented programming language such as Java, Scala, Smalltalk, Eiffel, JADE, Emerald, C++, C #, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

We claim:

1. A system, comprising
a non-transitory computer-readable storage medium storing executable instructions, and
at least one processor in communication with the non-transitory computer-readable storage medium, when executing the executable instructions, causing the system to implement a method, comprising:
obtaining first projection data relating to a region of interest (ROI) of a subject, the first projection data corresponding to a first equivalent dose level;
obtaining an image reconstruction model using an iterative algorithm, the image reconstruction model being constructed based on at least one of a first statistical model of noises in a projection domain or a second statistical model of noises in an image domain;
processing, based on the first statistical model of noises and a denoising model, the first projection data to obtain second projection data;
generating, based on the second projection data, a first image; and
determining, based on the first image and the second statistical model, the target image relating to the ROI of the subject, the target image corresponding to a second equivalent dose level higher than the first equivalent dose level, wherein the denoising model includes a parameter configured to adjust a strength of denoising the first projection data that is controlled by the first statistical model of noises.

2. The system of claim 1, wherein the method further includes:
   determining, based on the target image, first information relating to the ROI of the subject;
   obtaining second information relating to the ROI in a treatment plan of the subject; and
   performing at least one of operations based on at least one of the first information or the second information, wherein the operations include:
      performing a delivery of treatment radiation beam on the subject;
      determining a treatment plan of the subject;
      modifying the treatment plan of the subject; and
      adjusting a position of the subject in space.

3. The system of claim 1, wherein the processing, based on the first statistical model of noises and a denoising model, the first projection data to obtain the second projection data includes:
   determining, based on the first statistical model of noises, the denoising model; and
   denoising the first projection data using the denoising model to obtain the second projection data.

4. The system of claim 1, wherein the determining, based on the first image and the second statistical model, the target image relating to the ROI of the subject includes:
   determining, based on the second statistical model of noises, a second denoising model; and
   denoising the first image using the second denoising model to obtain the target image.

5. The system of claim 4, wherein the second denoising model includes a parameter configured to adjust a strength of denoising the first image that is controlled by the second statistical model of noises.

6. The system of claim 1, wherein the first equivalent dose level is no less than 15% of the second equivalent dose level.

7. The system of claim 1, wherein the first equivalent dose level is no less than 50% of the second equivalent dose level.

8. The system of claim 1, wherein the first equivalent dose level is no less than 85% of the second equivalent dose level.

9. The system of claim 1, wherein a ratio of the first equivalent dose level to the second equivalent dose level is equal to 1:7.

10. A method, implemented on a computing device having at least one processor and at least one non-transitory computer-readable storage medium, the method comprising:
   obtaining first projection data relating to a region of interest (ROI) of a subject, the first projection data corresponding to a first equivalent dose level;
   obtaining an image reconstruction model using an iterative algorithm, the image reconstruction model being constructed based on at least one of a first statistical model of noises in a projection domain or a second statistical model of noises in an image domain;
   processing, based on the first statistical model of noises and a denoising model, the first projection data to obtain second projection data;
   generating, based on the second projection data, a first image; and
   determining, based on the first image and the second statistical model, the target image relating to the ROI of the subject, the target image corresponding to a second equivalent dose level higher than the first equivalent dose level, wherein the denoising model includes a parameter configured to adjust a strength of denoising the first projection data that is controlled by the first statistical model of noises.

11. The method of claim 10, wherein the method further includes:
   determining, based on the target image, first information relating to the ROI of the subject;
   obtaining second information relating to the ROI in a treatment plan of the subject; and
   performing at least one of operations based on at least one of the first information or the second information, wherein the operations include:
      performing a delivery of treatment radiation beam on the subject;
      determining a treatment plan of the subject;
      modifying the treatment plan of the subject; and
      adjusting a position of the subject in space.

12. The method of claim 10, wherein the processing, based on the first statistical model of noises and a denoising model, the first projection data to obtain the second projection data includes:
   determining, based on the first statistical model of noises, the denoising model; and
   denoising the first projection data using the denoising model to obtain the second projection data.

13. The method of claim 10, wherein the determining, based on the first image and the second statistical model, the target image relating to the ROI of the subject includes:
   determining, based on the second statistical model of noises, a second denoising model; and
   denoising the first image using the second denoising model to obtain the target image.

14. The method of claim 13, wherein the second denoising model includes a parameter configured to adjust a strength of denoising the first image that is controlled by the second statistical model of noises.

15. The method of claim 10, wherein the first equivalent dose level is no less than 15% of the second equivalent dose level.

16. The method of claim 10, wherein the first equivalent dose level is no less than 50% of the second equivalent dose level.

17. The method of claim 10, wherein the first equivalent dose level is no less than 85% of the second equivalent dose level.

18. The method of claim 10, wherein a ratio of the first equivalent dose level to the second equivalent dose level is equal to 1:7.

19. A non-transitory computer readable medium, comprising:
   instructions being executed by at least one processor, causing the at least one processor to implement a method, comprising:
      obtaining first projection data relating to a region of interest (ROI) of a subject, the first projection data corresponding to a first equivalent dose level;
      obtaining an image reconstruction model using an iterative algorithm, the image reconstruction model being constructed based on at least one of a first statistical model of noises in a projection domain or a second statistical model of noises in an image domain;
      processing, based on the first statistical model of noises and a denoising model, the first projection data to obtain second projection data;
      generating, based on the second projection data, a first image; and determining, based on the first image and the second statistical model, the target image relating to the ROI of the subject, the target image corresponding to a second equivalent dose level higher than the first equivalent dose level, wherein the denoising model includes a parameter configured to adjust a strength of denoising the first projection data that is controlled by the first statistical model of noises.

20. The non-transitory computer readable medium of claim 19, further including:
   determining, based on the target image, first information relating to the ROI of the subject;
   obtaining second information relating to the ROI in a treatment plan of the subject; and
   performing at least one of operations based on at least one of the first information or the second information, wherein the operations include:
   performing a delivery of treatment radiation beam on the subject;
   determining a treatment plan of the subject;
   modifying the treatment plan of the subject; and
   adjusting a position of the subject in space.

* * * * *